United States Patent [19]
Walker et al.

[11] Patent Number: 5,041,974
[45] Date of Patent: Aug. 20, 1991

[54] MULTICHANNEL STIMULATOR FOR TUNED STIMULATION

[76] Inventors: Judith B. Walker, 881 Alma Real Dr., Ste. 110, Pacific Palisades, Calif. 90272; Michael S. Morse, 237 Payne St., Auburn, Ala. 36830

[21] Appl. No.: 263,789

[22] Filed: Oct. 26, 1988

[51] Int. Cl.⁵ .............................................. A61N 1/18
[52] U.S. Cl. ............................... 364/413.27; 128/421
[58] Field of Search .............. 364/413.27; 128/419 D, 128/419 PG, 420 A, 421, 422

[56] References Cited

U.S. PATENT DOCUMENTS

| | | | |
|---|---|---|---|
| 3,586,791 | 6/1971 | Puharich | 128/420.5 |
| 3,841,305 | 10/1974 | Hallgren | 128/419 R X |
| 4,232,679 | 11/1980 | Schulman | 128/419 PG |
| 4,390,023 | 6/1983 | Rise | 128/421 |
| 4,390,756 | 6/1983 | Hoffmann et al. | 128/419 R |
| 4,595,010 | 6/1986 | Radke | 128/421 |
| 4,598,713 | 7/1986 | Hansjürgens et al. | 128/421 |
| 4,613,937 | 9/1986 | Batty, Jr. | 364/413.27 |
| 4,635,639 | 1/1987 | Hakala et al. | 128/419 D |
| 4,640,286 | 2/1987 | Thomson | 128/421 |
| 4,642,769 | 2/1987 | Petrofsky | 364/413.27 |
| 4,686,991 | 8/1987 | Dufresne et al. | 128/421 |
| 4,688,574 | 8/1987 | Dufresne et al. | 128/421 |
| 4,690,145 | 9/1987 | King-Smith et al. | 128/421 |
| 4,699,143 | 10/1987 | Dufresne et al. | 128/419 R |
| 4,706,674 | 11/1987 | Dieken et al. | 363/37 |
| 4,712,558 | 12/1987 | Kidd et al. | 128/421 |
| 4,723,552 | 2/1988 | Kenyon et al. | 128/421 |
| 4,724,842 | 2/1988 | Charters | 128/423 W |
| 4,832,033 | 5/1989 | Maher et al. | 128/421 |

OTHER PUBLICATIONS

J. Allin & G. Inbar, FNS Control Schemes for the Upper Limb, IEEE Transactions on Biomedical Engineering, vol. BME-33, No. 9, pp. 818–828, Sep. 1986.
*Encyclopedia of Computer Science and Engineering,* Van Nostrand Reinhold Company, Inc., 1983, pp. 563–565.
J. Allin & G. Inbar, FNS Parameter Selection and Upper Limb Characterization, IEEE Transactions on Biomedical Engineering, vol. BME-33, No. 9, pp. 809–817, Sep. 1986.
Morse, "Multiple Channel, Parametrically Controlled, computerized Stimulation System", *Journal of Clinical Engineering,* vol. 15, No. 1, pp. 53–60 (abstract only).
A. Ishida & S. Miyazaki, Maximum Likelihood Identification of a Posture Control System, IEEE Transactions on Biomedical Engineering, vol. BME-34, No. 1, pp. 1–5, Jan. 1987.
H. Chizeck, P. Crago & L. Kofman, Robust Closed--Loop of Isometric Muscle Force Using Pulsewidth Modulation, IEEE Transactions on Biomedical Engineering, vol. 35, No. 7, pp. 510–517, Jul. 1988.
P. Crago, J. Van Der Meulen & J. Reswick, A Pilot Study of the Effects of Functional Electrical Stimulation on the Recovery of Function Following Stroke in Man, Functional Electrical Stimulation Applications in Neutral Prothesis, pp. 99–103, 1977.

(List continued on next page.)

*Primary Examiner*—Jerry Smith
*Assistant Examiner*—David Huntley

[57] ABSTRACT

A multichannel stimulator device has a host user interface circuit for enabling a user to select a channel and easily create and display a stimulus wave signal for the selected channel and generate a data signal specifiying the channel and stimulus wave signal. The stimulator also includes a master circuit for receiving the data signal and directing it to the specified channel as a wave building instruction signal. A slave circuit associated with the channel specified receives the wave building signal and responds by generating a corresponding low power stimulus wave signal in the channel specified. Then an output circuit coupled to the slave circuit electrically isolates the low power stimulus wave signal from other channels, amplifying and converting it to a corresponding high fidelity current stimulus wave signal.

13 Claims, 10 Drawing Sheets

SYSTEM OVERVIEW— STIMULATOR

OTHER PUBLICATIONS

P. Crago, P. Peckman & G. Thrope, Modulation of Muscle Force by Recruitment During Intramuscular Stimulation, IEEE Transactions on Biomedical Engineering, vol. BME-27, No. 12, pp. 679-684, Dec. 1980.

P. Crago, P. Peckman, J. Mortimer & J. Van Der Meulen, The Choice of Pulse Duration for Chronic Electrical Stimulation via Surface, Nerve, and Intramuscular Electrodes, Annals of Biomedical Engineering, pp. 252-264, 1974.

P. Crago, H. Chizeck, M. Neuman, & F. Hambrecht, Sensors For Use With Functional Neuromuscular Stimulation, IEEE Transactions on Biomedical Engineering, vol. BME-33, No. 1, pp. 256-267, Jan. 1986.

P. Crago, J. Mortimer & P. Peckham, Closed-Loop Control of Force During Electrical Stimulation of Muscle, IEEE Transactions on Biomedical Engineering, vol. 27, No. 6, pp. 306-311, Jun. 1980.

C. De Luca, Physiology & Mathematics of Myoelectric Signals, IEEE Transactions on Biomedical Engineering, vol. BME-26, No. 6, pp. 313-325, Jun. 1979.

M. Dimitrijevic, F. Gracanin, T. Prevec & J. Trontelj, Electronic Control of Paralyzed Extremities, Bio-Medical Engineering, pp. 8-14, Jan. 1967.

P. Gorman & J. Mortimer, The Effect of Stimulus Parameters on the Recruitment Characteristics of Direct Nerve Stimulation, IEEE Transactions on Biomedical Engineering, vol. BME-30, pp. 407-414, Jul. 1983.

F. Gracanin, E. Vavken, A. Jeglio & M. Benedik, Functional Stimulation, Advances in External Control of Human Extremities, pp. 529-534, 1973.

F. Gracanin & I. Marineek, Development of New Systems for Functional Electrical Stimulation, (Yugoslavia).

A. Kahn & T. Maveus, Technical Aspects of Electrical Stimulation Devices, Medical Progress through Technology, pp. 58-68, 1972.

A. Kralj, T. Bajd & R. Turk, Electrical Stimulation Providing Functional Use of Paraplegic Patient Muscles, Medical Progress through Technology, pp. 1-9, 1980.

A. Kralj & L. Vodovnik, Functional Electrical Stimulation of the Extremities: Part 1, Journal of Medical Engineering and Technology, pp. 12-15, Jan. 77.

A. Kralj & L. Vodovnik, Functional Electrical Stimulation of the Extremities: Part 2, Journal of Medical Engineering and Technology, pp. 75-80, Mar. 1977.

W. Liberson, H. Holmqust, D. Scot & M. Dow, Functional Electrotherapy: Stimulation of the Peroneal Nerve Synchronized with the Swing Phase of the Gait of Hemiplegic Patients, Archives of Physical Medicine & Rehabilitation, pp. 101-105, Feb. 1961.

A. Livnat, R. Johnson & J. Zehr, Programmable Miniature Backpack Stimulator for Chronic Biomedical Studies, IEEE Transactions on Biomedical Engineering, vol. BME-28, No. 4, pp. 359-362, Apr. 1981.

E. Marsolais, R. Kobetic, H. Chizeck & R. Lew, Advances in Paraplegic Walking Using Electrical Stimulation, Presentation at American Spinal Injury Association Conference, Apr. 16, 1985.

E. Marsolais & R. Kobetic, Functional Walking in Paralyzed Patients by Means of Electrical Stimulation, Clinical Orthopaedics and Related Research, No. 175, pp. 30-36, May 1983.

E. Marsolais & A. Massiello, Finger Switch For A Portable Micropressor System to Restore Walking in Paraplegics, RESNA 8th Conference, 1985.

E. Marsolais & R. Kobetic, Criteria For Practical FNS Systems For Paralyzed People, Source and Date Unknown.

E. Marsolais & R. Kobetic, Experience with A Helical Percutaneous Electrode in The Human Lower Extremity, RESNA 8th Annual Conference, 1985.

J. Mortimer, D. Kaufman & U. Roessman, Intramuscular Electrical Stimulation: Tissue Damage, Annals of Biomedical Engineering, vol. 8, pp. 235-244, 1980.

W. Nix & M. Dahm, The Effect of Isometric Short-Term Electrical Stimulation on Denervated Muscle, Muscle & Nerve, vol. 10, pp. 136-143, Feb. 1987.

P. Peckham & J. Mortimer, Restoration of Hand Function in the Quadriplegic Through Electrical Stimulation, Functional Electrical Stimulation Appl. in Neutral Prostheses, Hambrecht & Reswick, pp. 83-95, 1977.

P. Peckham, J. Van Der Meulen & J. B. Reswick, Electrical Activation of Skeletal Muscle by Sequential Stimulation, Functional Electrical Stimulation Appl. in Neutral Prothesis, pp. 45-49, 1977.

(List continued on next page.)

OTHER PUBLICATIONS

P. Peckham, Functional Electrical Stimulation: Current Status and Future Prospects of Applications to the Neuromuscular System in Spinal Cord Injury, Paraplegia, vol. 25, pp. 279-288, 1987.

P. Peckham, J. Mortimer & E. Marsolais, Controlled Prehension and Release in the C5 Quadriplegic Elicited by Functional Electrical Stimulation of the Paralyzed Forearm Musculature, Annals of Biomedical Engineering, vol. 8, pp. 369-388, 1980.

P. Peckham, E. Marsolais & J. Mortimer, Restoration of Key Grip and Release in the C6 Tetraplegic Patient Through Functional Electrical Stimulation, The Journal of Hand Surgery, vol. 5, No. 5, pp. 462-469, Sep. 1980.

D. Peterson & H. Chizeck, Linear Quadratic Control of a Loaded Agonist-Antagonist Muscle Pair, IEEE Transactions on Biomedical Engineering, vol. BME-34, No. 10, pp. 790-796, Oct. 1987.

J. Petrofsky, Control of the Recruitment and Firing Frequencies of Motor Units in Electrically Stimulated Muscles in the Cat, Medical & Biological Engineering & Computing, pp. 302-308, May 1978.

J. Petrofsky, Digital-Analogue Hybrid 3-Channel Sequential Stimulator, Medical & Biological Engineering & Computing, pp. 421-424, May 1979.

J. Petrofsky, C. Phillips & H. Heaton, III, Feedback Control System for Walking in Man, Computers in Biology and Medicine, No. 2, vol. 14, pp. 135-149, 1984.

L. Seligman, Physiological Stimulators: From Electric Fish to Programmable Implants, IEEE Transactions on Biomedical Engineering, vol. BME-29, No. 4, pp. 270-283, Apr. 1982.

B. Smith, P. Peckham, M. Keith & D. Roscoe, An Externally Powered, Multichannel, Implantable Stimulator for Versatile Control of Paralyzed Muscle, IEEE Transactions on Biomedical Engineering, vol. BME-34, No. 7, Jul. 1987.

M. Solomonow, E. Eldred, J. Lyman & J. Foster, A New Technique for Functional Neuromuscular Stimulation, Advances in Control of Human Extremities, Belgrade 1978, pp. 47-62.

M. Solomonow, Fatigue Optimal Selective Electroblock Parameters in the Linear Control of Paralyzed Muscle Force, Advances in Control of Human Extremities, Belgrade 1981, pp. 139-144.

M. Solomonow, E. Eldred & J. Lyman, Electrically Induced Recruitment in Paralyzed Muscles: A Progress Report, Manuscript, pp. 1-25, Sept. 10, 1979.

M. Solomonow, External Control of the Neuromuscular System, IEEE Transactions on Biomedical Engineering, vol. BME-31, No. 12, pp. 752-763, Dec. 1984.

L. Streeter, H. Chizeck & R. Kobetic, Input-Output Response of The Quadriceps Muscle in Paralegic Patients, RESNA 8th Conference, 1985.

P. Strojnik, A. Kralj & I. Ursic, Programmed Six-Channel Electrical Stimulator for Complex Stimulation of Leg Muscles During Walking, IEEE Transactions on Biomedical Engineering, vol. BME-2, No. 2, pp. 112-116, Feb. 1979.

G. Thrope, P. Peckham & P. Crago, A Computer-Controlled Multichannel Stimulation System for Laboratory Use in Functional Neuromuscular Stimulation, IEEE Transactions on Biomedical Engineering, vol. 32, No. 6, pp. 363-370, Jun. 1985.

C. Van Den Honert & J. Mortimer, The Response of the Myelinated Nerve Fiber to Short Duration Biphasic Stimulating Current, Annals of Biomedical Engineering, vol. 7, pp. 117-125, 1979.

L. Vodovnik, C. Long II, E. Regenos & A. Lippay, Pain Response to Different Tetanizing Currents, Archives of Physical Medicine & Rehabilitation, pp. 187-197, Feb. 1965.

L. Vodonik, F. Gracanin, S. Rebersek & M. Stefancic, Long Term Effects of Functional Electrical Stimulation, Advances in External Control of Human Extremities, pp. 529-534, 1973.

I. Vodovnik, V. Valenecic, M. Stefaneic, T. Jenjkan, F. Gracanin, Functional Electrical Stimulation of Denervated Muscles, Advances in External Control of Human Extremities Conference, Belgrade 1981, pp. 103-110, 1981.

SYSTEM OVERVIEW—STIMULATOR

FIG. 3

Fig. 4  MASTER LAYOUT

Fig. 5 SLAVE LAYOUT

FIG. 6 — ISOLATION AND AMPLIFICATION

Fig. 8A — A. HOST COMPUTER TO MASTER UNIT
1. CHANNEL & OP CODE WORD (8 BITS)

| 7 | 6 | 5 | 4 | 3 | 2 | 1 | 0 |
|---|---|---|---|---|---|---|---|
| 0 | 0 | 1 | 0 | 0 | 1 | 0 | 0 |

CHANNEL 4 BITS — OP CODE 4 BITS

Fig. 8B — 2. DATA WORD (8 BITS)

| 7 | 6 | 5 | 4 | 3 | 2 | 1 | 0 |
|---|---|---|---|---|---|---|---|
| 0 | 1 | 0 | 0 | 1 | 0 | 1 | 0 |

Fig. 8C — B. MASTER UNIT TO SLAVE UNIT
1. OP CODE WORD (8 BITS) (FOR SYSTEM BUS DATA LINES)

| 7 | 6 | 5 | 4 | 3 | 2 | 1 | 0 |
|---|---|---|---|---|---|---|---|
| 0 | 0 | 0 | 0 | 0 | 1 | 0 | 0 |

Fig. 8D — 2. CHANNEL CODE WORD (8 BITS) (FOR SYSTEM BUS ADDRESS LINES)

| 7 | 6 | 5 | 4 | 3 | 2 | 1 | 0 |
|---|---|---|---|---|---|---|---|
| 0 | 0 | 0 | 0 | 0 | 1 | 0 | 0 |

Fig. 8E — 3. DATA WORD (8 BITS) (FOR SYSTEM BUS DATA LINES)

| 7 | 6 | 5 | 4 | 3 | 2 | 1 | 0 |
|---|---|---|---|---|---|---|---|
| 0 | 1 | 0 | 0 | 1 | 0 | 1 | 0 |

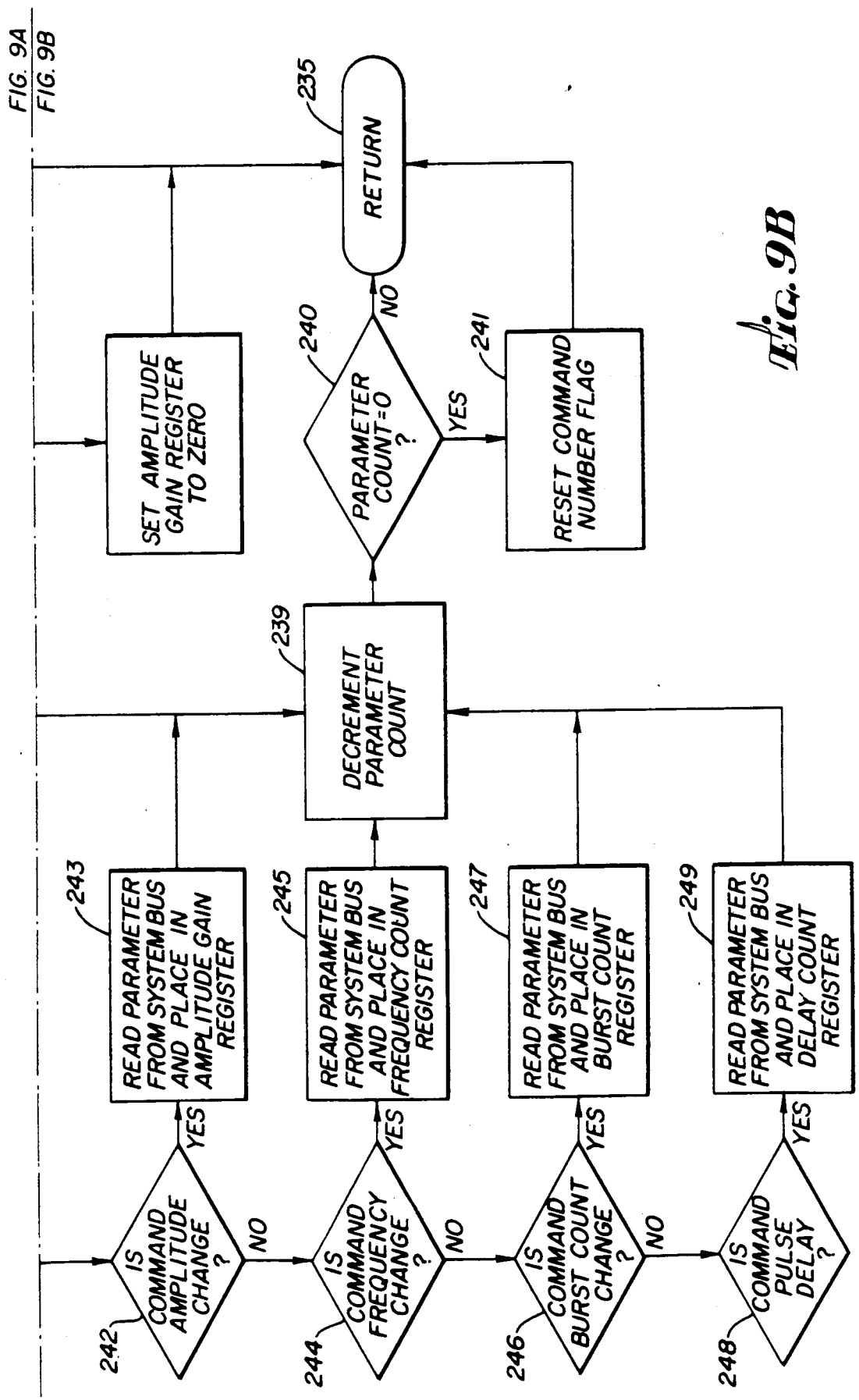

MULTICHANNEL STIMULATOR FOR TUNED STIMULATION

The invention relates to electrical pulse generators for stimulating biological tissue, and more particularly to a multichannel stimulator for producing controlled current pulses to be applied to animals and humans.

Stimulators that can deliver a controlled electrical pulse to living tissue have been found to have a number of uses for research, therapy, and rehabilitation for animals and humans. For example, when suitably applied to excite nerve fibers such pulses can mask or reduce pain from injuries, elicit sensory responses, and stimulate muscle activity not otherwise possible because of injuries.

One particularly promising application is for restoring muscle tone and function, such as grasping and walking, in humans paralyzed by spinal cord injuries and the like. Such muscle stimulation strong enough to elicit a coordinated limb movement is called functional electric stimulation (FES). In one type of FES, controlled current pulses are applied via a pair of surface electrodes on the patient's skin for nerve stimulation of the underlying tissue.

Multichannel stimulators that can deliver different, synchronized pulses to a plurality of electrode pairs at different muscle sites are particularly useful for stimulating coordinated limb movement. Such multichannel stimulators can also be used to treat a number of different patients at the same time, increasing the efficiency of staff and equipment.

However, there are a number of difficulties with such artificial electrical stimulation. Often it is very painful to the subject and frequently the stimulated muscles experience fatigue, reducing or even stopping their response to the electrical stimulus. This is not surprising when one considers that often the applied stimulus waveform is only a crude approximation, such as a spike or biphasic waveform, of those produced naturally in a healthy organism. Moreover, it may be that an injured organism requires a special waveform shape customized to compensate for the particular injury, etc.

To experiment to reduce these problems, researchers would like to experiment more freely with the custom shaping or tuning of the applied waveform and its various parameters. They would also like to have a number of channels available for this purpose.

Conventional stimulators are not well adapted for such experimentation to customize or tune the applied waveform. Small portable units usually have only a limited selection of predetermined, normalized waveform shapes that can be scaled in time, amplitude, and frequency of repetition. They do not enable the user to create a new shape "on the fly". Moreover, their predetermined normalized waveform shapes are selected by the maker of the stimulator rather the user.

Larger stimulators, such as those that use a minicomputer or the like have other disappointing limitations for a user physician or therapist. Typically, they have a single central processing unit (CPU), that must divide its time between the user interface, computing waveforms for a number of channels, and coordinating the signals. As the number of channels grows, there is an increasing burden on the single CPU. Therefore, to save CPU time, such larger devices also usually rely on a limited repertoire of standardized waveforms and provide a user interface more technical than user friendly.

Yet a further problem arises because multichannel stimulators of whatever size must be designed to avoid leakage currents between unpaired electrodes of different channels, since such leakage produces undesirable crosstalk between channels. The conventional way to isolate each channel is for the signal produced by the stimulator to be passed through an isolation transformer before being output. However, conventional isolation transformers of reasonable price are of low fidelity, distorting and even clipping the stimulus signal. Thus, the stimulus pulses of conventional multichannel stimulators often output pulse shapes that are distorted from the ideal and difficult to shape precisely.

Accordingly, it is an object of the invention to provide a multichannel stimulator that enables the user great freedom to create or tune the normalized waveshape used in each channel, to adjust its parameters, and to adjust the coordination timing between the waveforms in different channels.

Another object of the invention is to provide a multichannel stimulator with a user-friendly interface for creating or tuning the normalized waveshape used in each channel, adjusting its parameters, and adjusting the relative timing between the waveforms in different channels.

Another object of the invention is to provide a multichannel computerized stimulator with both a central master processor for coordination and a separate processor for each channel to enable a large number of channels to be used without degrading overall stimulator performance.

Yet another object of the invention is to provide a multichannel stimulator which maintains excellent electrical isolation between different channels but also produces the stimulus signals desired by the user with high fidelity.

Further objects and advantages will be apparent from the following description and the accompanying drawings.

SUMMARY OF THE INVENTION

A multichannel stimulator device has a host user interface circuit for enabling a user to select a channel and easily create and display a stimulus wave signal for the selected channel and generate a data signal specifying the channel and stimulus wave signal. The stimulator also includes a master circuit for receiving the data signal and directing it to the specified channel as a wave building instruction signal. A slave circuit associated with the channel specified receives the wave building signal and responds by generating a corresponding low power stimulus wave signal in the channel specified. Then an output circuit coupled to the slave circuit electrically isolates the low power stimulus wave signal from other channels, amplifying and converting it to a corresponding high fidelity current stimulus wave signal.

BRIEF DESCRIPTION OF THE DRAWINGS

FIG. 3 is a user interface display produced by the stimulator of FIG. 1.

FIGS. 8a–8e are charts of the signal codes sent between a host computer master unit, slave unit of the stimulator of FIG. 1.

DESCRIPTION OF THE PREFERRED EMBODIMENT

Figure 1:
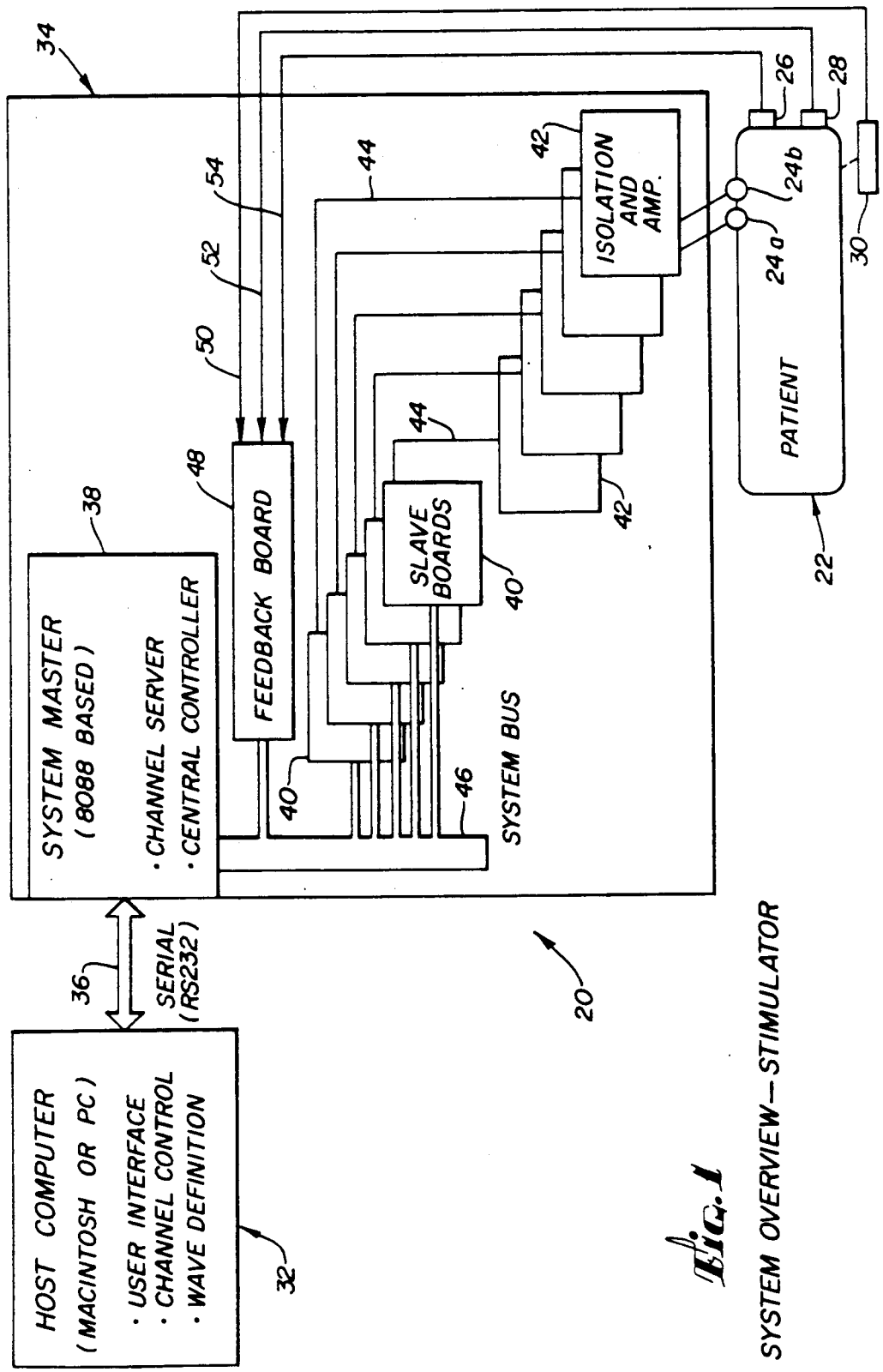
FIG. 1 is a functional block diagram of a multichannel stimulator in accordance with an embodiment of the present invention, shown coupled to a patient.

FIG. 1 is a functional block diagram of a multichannel electrical stimulator 20 in accordance with an embodiment of the present invention. Stimulator 20 is coupled to an animal or human organism, such as a patient 22, by at least one pair of electrodes 24a and 24b making electrical contact with the patient.

While stimulator 20 may be operated open loop, if feedback is desired, sensors 26 and 28, such as position, pressure, or motion sensors for monitoring muscle movements, can be attached to patient 22 or her limbs. Sensor 30 represents another form of feedback sensor, such as an electric eye which measures a position of patient 22 or her limbs without necessarily being attached to the patient.

If the user, generally a physician or therapist separate from the patient, wishes to make adjustments to the electrical pulses from stimulator 22, a suitably programmed host microcomputer 32 including a display, such as a Macintosh or IBM PC, can be provided as user friendly interface. That is, the host microcomputer 32, which has its own processor, memory, and display, can be programmed to provide status information to the user and to accept and echo back user input selections.

The stimulus signals are produced by a system unit 34 which can be coupled for two-way signal communication with host computer 32, such as by a two-way RS-232 serial interface 36. Generally, Macintosh or PC microcomputer host 32, will come standard with or can easily be adapted to have a two-way RS-232 serial port (not shown). Therefore, in system unit 34 a matching RS232 serial port may also be provided, the serial ports respectively on host 32 and system unit 34 being wired together by a null modem cable or the like to form interface 36. Two-way interface 36 enables selections or commands entered by the user on the host microcomputer 32 to be transmitted to system unit 34, and also enables system unit 34 to report status or feedback to the user via host 32. A serial communication speed of 300 bits/sec, or greater, will generally be sufficient for this purpose.

System unit 34 includes a microprocessor-based system master unit 38 coupled by a system bus 46 to a number of microprocessor-based slave units or boards 40, one slave for each channel. Each slave unit 40 in turn is coupled by a connection 42 to a corresponding isolation and amplification unit 42. Each unit 44 amplifies the channel signal it receives, producing a current pulse of like shape at an output for a corresponding pair of patient electrodes 24a, 24b.

For simplicity, only of the units 42 is shown coupled to a pair of electrodes 24a, 24b which are in turn electrically coupled to patient 22. However, it is to be understood that when the unit 42 of each channel is used, a corresponding different pair of electrodes 24a, 24b for that channel are wired to the unit 42 and then electrically coupled to the patient.

System master unit 38 is coupled to serial interface 36 to receive user selected commands from host computer 32 and send the host computer status or feedback information for display to the user. In response to the user commands, System master unit 38 also sends commands and data to the appropriate slave unit, instructing it what signal shape to generate for the channel and coordinating the relative timing between the stimulus signals in the various channels by STOP, START, and GAIN commands.

Figure 2:
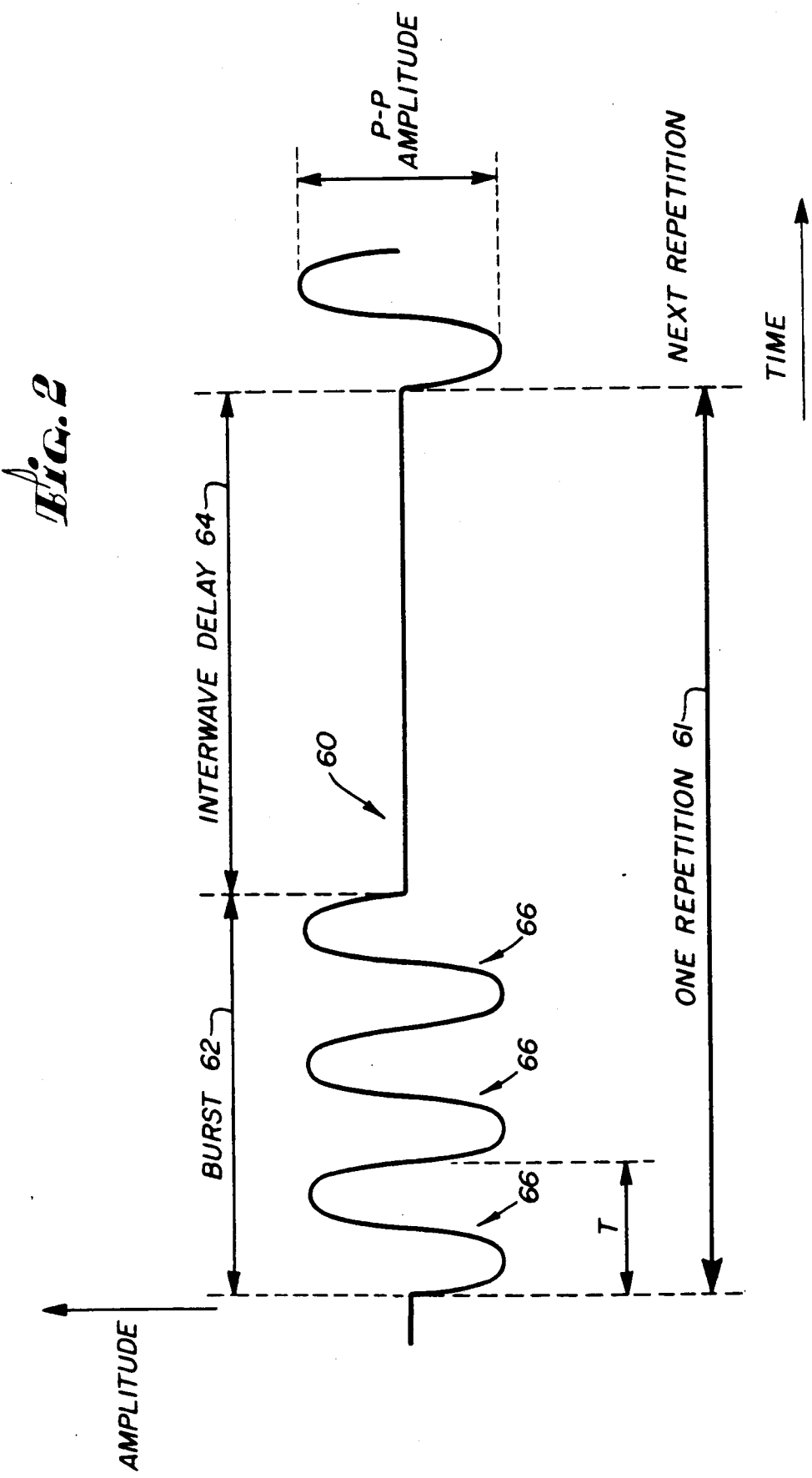
FIG. 2 is a graph of a typical repeating current pulse produced by the stimulator of FIG. 1 for an individual channel, showing pulse amplitude as a function of time.

FIG. 2 shows an example of the general type of stimulus signals to be produced in each channel by its corresponding slave unit 40. The output of a slave unit 40 of FIG. 1 is a voltage signal of the desired shape, which is converted to an appropriate current pulse by the corresponding isolation and amplification unit 42.

In the embodiment of FIG. 1, both master unit 38 and each slave unit 40 use a processor equivalent to the Intel 8088, such as an NEC V20 chip, though other suitable processors may be used. Thus, one microprocessor (in master 38) determines and communicates what signal will be generated in each channel, and a second microprocessor (in each slave 40) actually digitally generates the specified stimulus signal for that channel. The digital signal generated by a slave 40 is afterwards converted to analog by a suitable digital-to-analog converter (DAC), for example one included in slave unit 40.

The stimulator can be operated "open loop", that is, without feedback indicated how the patient is affected. However, if feedback is desired, the output from one or more patient monitoring sensors 26, 28 and 30 can be coupled to a feedback unit or board 48, which in turn is coupled to master unit 38 by system bus 46. Feedback unit 48 amplifies and interprets the feedback signals from the sensors for feedback to master unit 38 by means of polling or interrupts. Master unit 38 or the user (receiving the feedback via host computer 32) can then adjust the applied stimulus in response to the feedback information.

FIG. 2 shows the amplitude of a typical signal 60 generated by a slave unit 40 as a function of time. One repetition of signal 60 includes a burst portion 62 and an interwave delay 64, after which the signal may be repeated if desired as shown. Burst portion 62 in turn includes one or more repeats of a waveform 66 selected or designed by the user. By means of the user interface of host microcomputer 32, the user can determine:

(a) the normalized shape of waveform 66, by specifying the amplitude (quantized to 256 levels) at 50 equally spaced points along the waveform (b) the duration T of waveform 66 (by specifying a "frequency" in Hz=1/T); typically in a range of 0.2 ms to 0.5 sec (b) the gain applied to scale the waveform of (a); typically to produce an output at slave unit 40 of a maximum of +10 volts to −10 volts, which drives the output of isolation and amplification unit 42 to a maximum of +100 ma to −100 ma (b) the number of times N that waveform 66 appears in the burst 62; typically 1–65,536 (64K), though 1–100 is usually the range selected by users (c) the duration of interwave delay 64; typically 0-100 ms FIG. 3 illustrates a typical user interface display 70 produced by the stimulator of FIG. 1. This can be produced by programming host computer 32 in any convenient programming language for that machine. Appendix 1 to this application is a source program listing that shows how this can be done in a high level language for a Macintosh microcomputer, such as Microsoft Basic. The display only shows four active stimulus channels, but in fact the stimulator is constructed to easily accommodate up to 256 different channels. If more channels are used, the display can be switched between them by the user or "windows" opened in the display to view a desired channel.

In the display of FIG. 3, the stimulus signals 60 (see FIG. 2) produced by the corresponding slave 40 of channels 1-4 are shown at the right in corresponding boxes 72, 74, 76 and 78. As is well known, if a Macintosh microcomputer is used the standard interface will include a "mouse" cursor control or pointing device (not shown) moved by the user's hand to move a corresponding cursor in the display 70, such as cursor arrow 71. The mouse also has at least one pushbutton that the user can push or "click" (rapidly push and release) to select objects covered or pointed to by cursor arrow 71.

In display 70, if a channel (1, 2, 3 or 4) is active a corresponding dot on the display (80, 82, 84, 86) is black, inactive having a blank dot. Thus, in display 70 channels 1-3 are shown active, while channel 4 is inactive. To adjust the stimulus signal on a channel 1, 2, 3 or 4 the user clicks the mouse over a corresponding interaction box 80a, 82a, 84a, 86a, which then changes from blank to an "X". Only one channel can be activated at a time for adjustment by the user. In display 70 this is channel 1. The user then selects which signal parameter is to be adjusted by clicking on its designation.

For example, to alter the period T of the normalized waveform 66 (see FIG. 2) repeated in the burst portion 62, the user can click on the designation 90 "—1/T=Hz". This display shows that 1/T=1000 Hz (or T=1 ms). If she clicks on this item, a keyboard (not shown) of the host computer 32 will allow her to key in a change for the reading "1000". Similarly there are designations and readings for [Timeform] CYCLES 92, [Interwave] DELAY 64, % TForm 96, and [Manually Selected] Amplitude 98.

In addition having the corresponding slave build a repeating waveform 60 of the type shown in FIG. 2, host computer 32 can send a series of GAIN commands to the slave via master unit 38 so that the gain of the stimulus signal on selected channel will vary slowly (relative to one repetition of signal 60). For this control of the stimulus is shown for each channel in the corresponding elongated rectangles 81, 83, 85 and 87, each of which has a corresponding amplitude vs. time plot (TIME FORM or TFORM) 81a, 83a, 85a, 87a. Box 72 shows the stimulus signal being produced in channel 1, which has two 1 ms bipolar pulses per burst followed by a 18 ms delay; this indicates that the signal has a 20 ms (1+1+18) duration and is being repeated about 50 times/sec. Elongated rectangle 81 shows how the gain of this signal will vary on subsequent repetitions, from 0 to a peak after about 10 seconds, and then back to 0 after about 5 more seconds. The designation "TFDUR" at 106 has a reading of 28, which means that TIME FORM 81a takes 28 seconds from start to finish. The designation "TH" at 108 can be used to set a floor (or threshold) below which the GAIN of the TIME FORM will not be allowed to fall if desired. For example, if TH=10%, the signal of box 72 will be reduced at most to 10% of full signal strength, guaranteeing that it is continuously present and repeating.

Display 70 also has designations to start the Time Form (START 100) and stop it (STOP), to make the TIME FORM repeat automatically (CYCLIC) rather just appear once, to limit the maximum gain of the TIME FORM to some percentage (%TFORM 96) or for manual control of the GAIN of the waveforms of boxes 72, 74, 76 and 78.

If the user clicks on the WAVEFORM designation 112, a file containing the set of data for a desired normalized waveform can be selected from a menu (not shown) of those waveform files already stored on the disk drive of host computer 32, and the waveform displayed. From this menu the user can also modify and save to disk an existing normalized waveform or construct a new one entirely by indicating its shape with the mouse. The TIMEFORM designation 114 works similarly for retrieving modifying and creating TIME FORMS, while a FEEDBACK 115 choice allows the user to designate how host computer 32 should handle the feedback information from feedback board 48.

Figure 4:
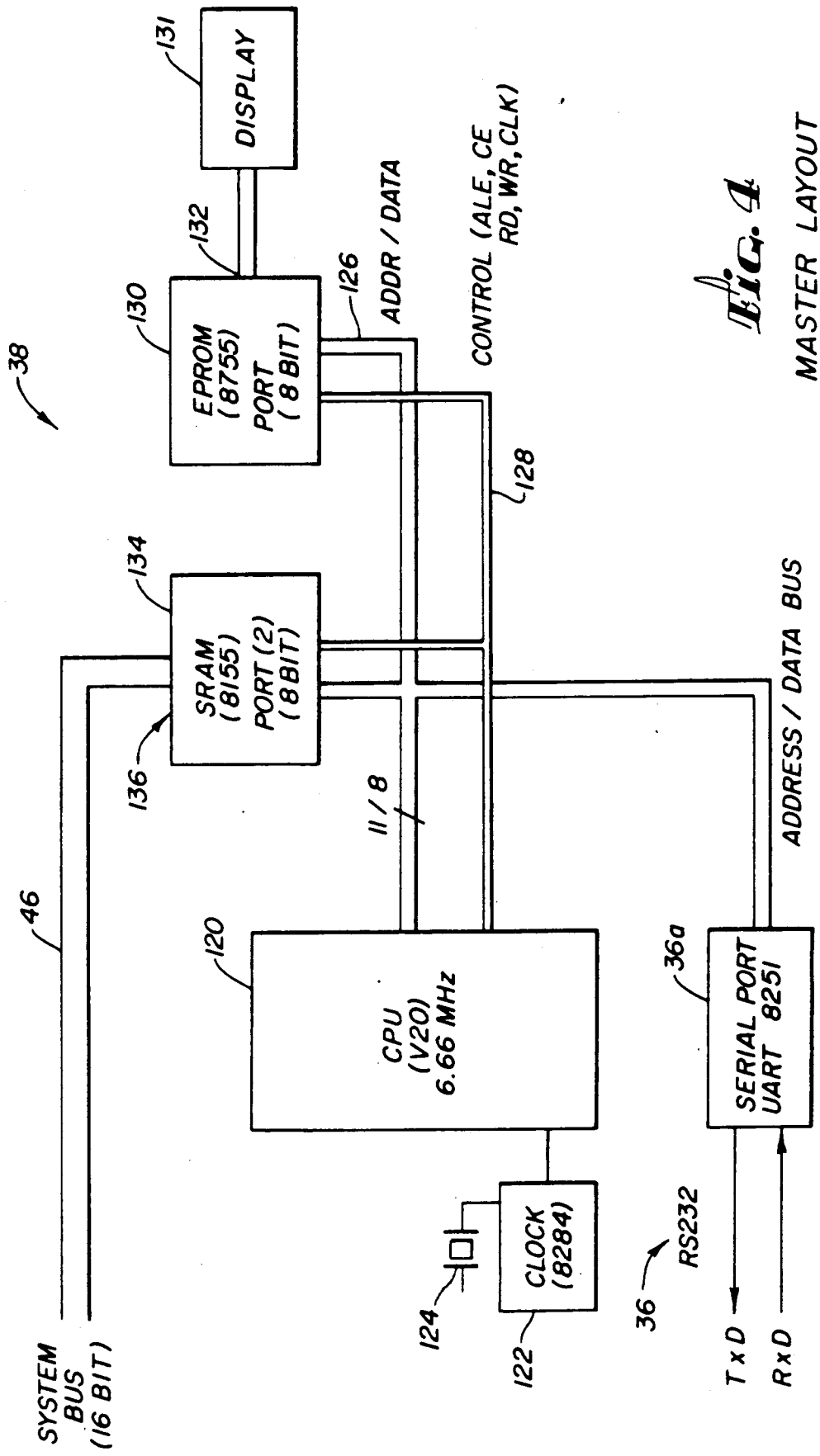
FIG. 4 is a functional block diagram of a system master unit of the multichannel stimulator of FIG. 1.

FIG. 4 is a functional block diagram of a system master unit 38 of the multichannel stimulator of FIG. 1. A microprocessor 120 has a clock 122 having crystal 124. In the preferred embodiment, microprocessor 120 is an equivalent of the popular 16 bit Intel 8088 microprocessor having an 8 bit data bus addressable by up to 20 address lines. For example, processor 120 can be an NEC V20 running at 6.66 MHz. Processor 120 has an address and data bus 126 allowing for 11 address bits and 8 data bits and a control bus 128. Buses 126 and 128 bidirectionally couple processor 120 to a ROM or EPROM 130 (for program storage) and a fast static RAM 136 for scratchpad memory.

As an example of the master unit program for microprocessor 120 stored in ROM 130, please refer to Appendix 2 to this application. Appendix 2 is a source program listing in assembly language for the Intel 8088, this particular assembly listing was prepared for a Universal Cross-Assembler used on a Digital Equipment VAX system.

Bus 126 also couples processor 120 to a UART 8251, supplying a serial port 36a for the serial interface 36 shown in FIG. 1. Processor 120 polls the serial port to deterine if host computer has sent it any instructions or data. FIG. 8 shows the form of the host to master signal codes and Table 1 lists typical values for them.

TABLE 1

| | OPERATION CODES AND CORRESPONDING DATA BYTES | | | |
|---|---|---|---|---|
| OP NAME | OP CODE (IN HEX) | OP CODE (IN BINARY) | NUMBER OF DATA BYTES FOLLOWING | MEANING OF DATA BYTES |
| START | 00h | 0000 | 0 | |
| FREQ (1/T) | 01h | 0001 | 2 | MSB, LSB |
| NO. OF CYCLES | 02h | 0010 | 2 | MSB, LSB |
| DELAY COUNT | 03h | 0011 | 2 | MSB, LSB |

TABLE 1 -continued

OPERATION CODES AND CORRESPONDING DATA BYTES

| OP NAME | OP CODE (IN HEX) | OP CODE (IN BINARY) | NUMBER OF DATA BYTES FOLLOWING | MEANING OF DATA BYTES |
| --- | --- | --- | --- | --- |
| WAVE SHAPE | 04h | 0100 | 50 | 00h = −2.5 V |
|  |  |  |  | 80h = 0 V |
|  |  |  |  | FFh = +2.5 V |
| GAIN | 05h | 0101 | 1 | 00h = −MAX |
|  |  |  |  | 80h = 0 |
|  |  |  |  | FFh = +MAX |
| RESET | 06h | 0110 | 1 | DATA BYTE |
| AUTOTEST | 07h | 0111 | 1 | DATA BYTE |
| SEND DATA | 08h | 1000 | 1 | DATA BYTE |
| STOP | 0Fh | 1111 | 0 |  |

Scratchpad RAM 134 can be realized by a 256 byte Intel 8155 memory chip which includes for convenience two eight bit I/O ports addressable by microprocessor 120. These two ports can be used to enable the microprocessor send or receive 16 bits of information on system bus 46, which is a 16 bit bus (8 address bits, 8 data bits).

Program-storing ROM 134 can be realized by a two kilobyte Intel 8755 memory chip which includes for convenience an eight bit I/O port addressable by microprocessor 120 This port can be used to enable the microprocessor send or receive 8 bits of data to an 8 segment display 121. Display 131 is optional, but if the display is provided the program of Appendix 2 has microprocessor 120 indicate status and progress information for monitoring, checking, and debugging the stimulator.

Figure 5:
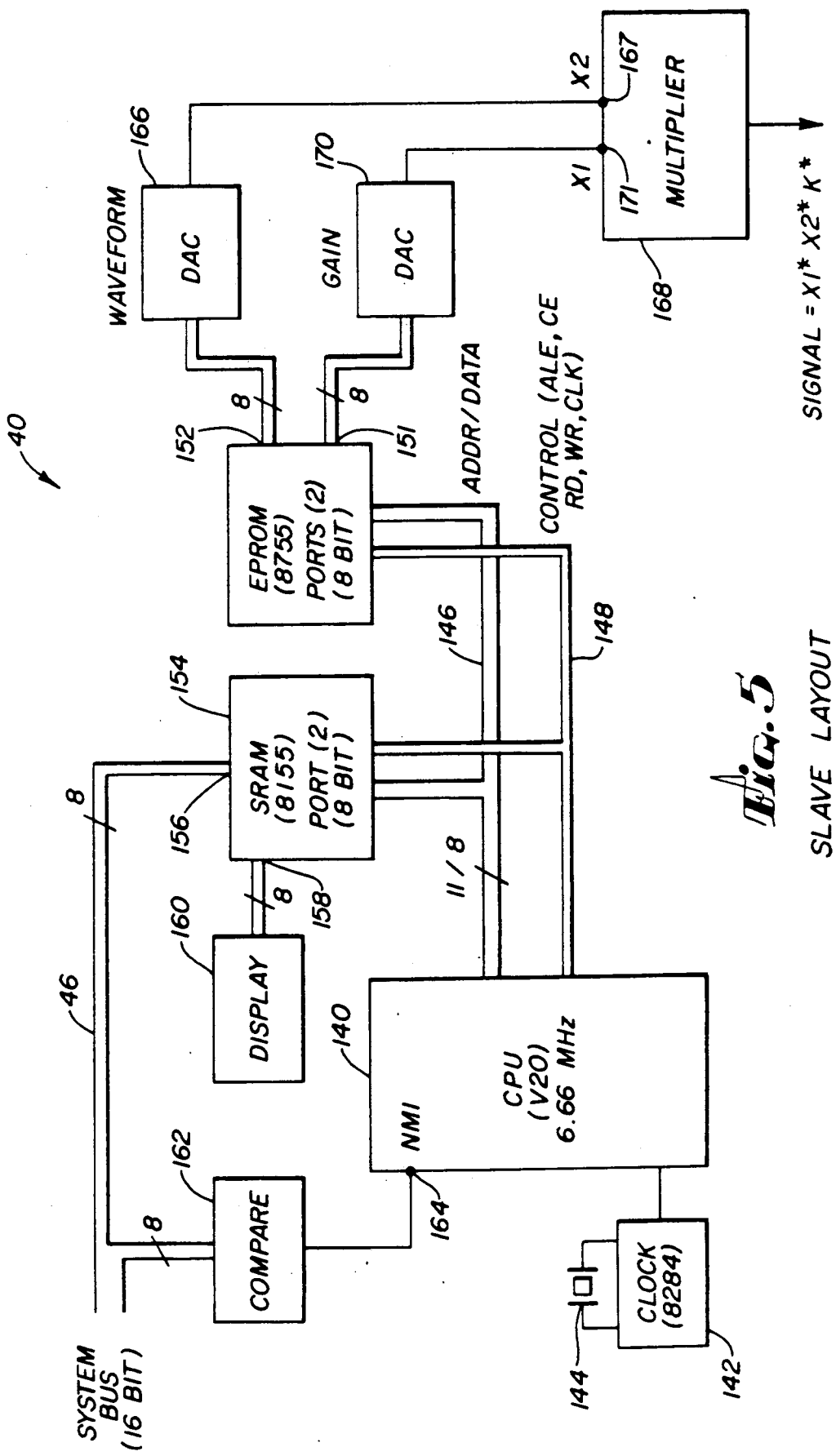
FIG. 5 is a functional block diagram of one of the slave units of the multichannel stimulator of FIG. 1.

FIG. 5 is a functional block diagram of a slave unit 40 of the multichannel stimulator of FIG. 1. A microprocessor 164 has a clock 142 having crystal 144. In the preferred embodiment, microprocessor 140 is also a NEC V20 running at 6.66 MHz. Therefore, processor 140 has an address and data bus 146 allowing for 11 address bits and 8 data bits and a control bus 148. Buses 146 and 148 bidirectionally couple processor 140 to a ROM or EPROM 150 (for program storage) and a fast static RAM 154 for scratchpad memory.

As an example of the slave unit program for microprocessor 140 stored in ROM 150, please refer to Appendix 3 to this application. Appendix 3 is a source program listing in assembly language for the Intel 8088.

Scratchpad RAM 154 can be realized by a 256 byte Intel 8155 memory chip which includes for convenience two eight bit I/O ports addressable by microprocessor 140. One of these ports can be used to enable microprocessor 140 to receive 8 data bits of information from system bus 46, which is a 16 bit bus (8 address bits, 8 data bits). The other port can couple processor 140 to an optional 8 segment single character display for debugging, etc.

Master unit 38 can send a particular slave 40 a wave-specifying command or data for its channel by putting an 8 bit data word on system bus 46 and then placing a prespecified eight bit binary address (e.g. channel 1 = 0000 0001, channel 2 = 0000 0010, etc.) on the system bus. Each slave unit 40 includes a comparator 162 which stores the slave's address code and compares it with the address on system bus 40; when there is a match comparator 162 sends a nonmaskable interrupt 164 to microprocessor 120, which branches to an interrupt routine for reading the data bits on bus 46 via the 8 bit port on board RAM chip 154. FIG. 8 shows the form of the master to host signal codes and Table 1 lists typical values for them.

Program-storing ROM 150 can be realized by a two kilobyte Intel 8755 memory chip which includes for convenience two eight bit I/O ports addressable by microprocessor 140. These ports can be used to enable microprocessor 140 to send 8 bit data words respectively to a waveform digital-to-analog converter (DAC) 166 and a gain DAC 170. The DAC's 166 and 170 are respectively coupled X2 and X1 inputs of a multiplier 168 to produce the output signal voltage of the slave.

Thus, microprocessor 140 in slave 40 digitally generates by means of the program of Appendix 3 a series of waveform signal levels according to data from the master unit 38 specifying the normalized a wave shape (50 points), burst number, frequency (=1/T), and interburst delay. From this data and the program it produces the digitalized amplitudes for the stimulus wave, sending them to DAC 166. Similarly, master unit 38 has also specified the instantaneous overall GAIN to be used by the slave, and this is output to DAC 170. The respective analog outputs from DAC's 166 and 177 are multiplied by multiplier 168 to give the desired amplitude of the waveform as a function of time.

Figure 6:
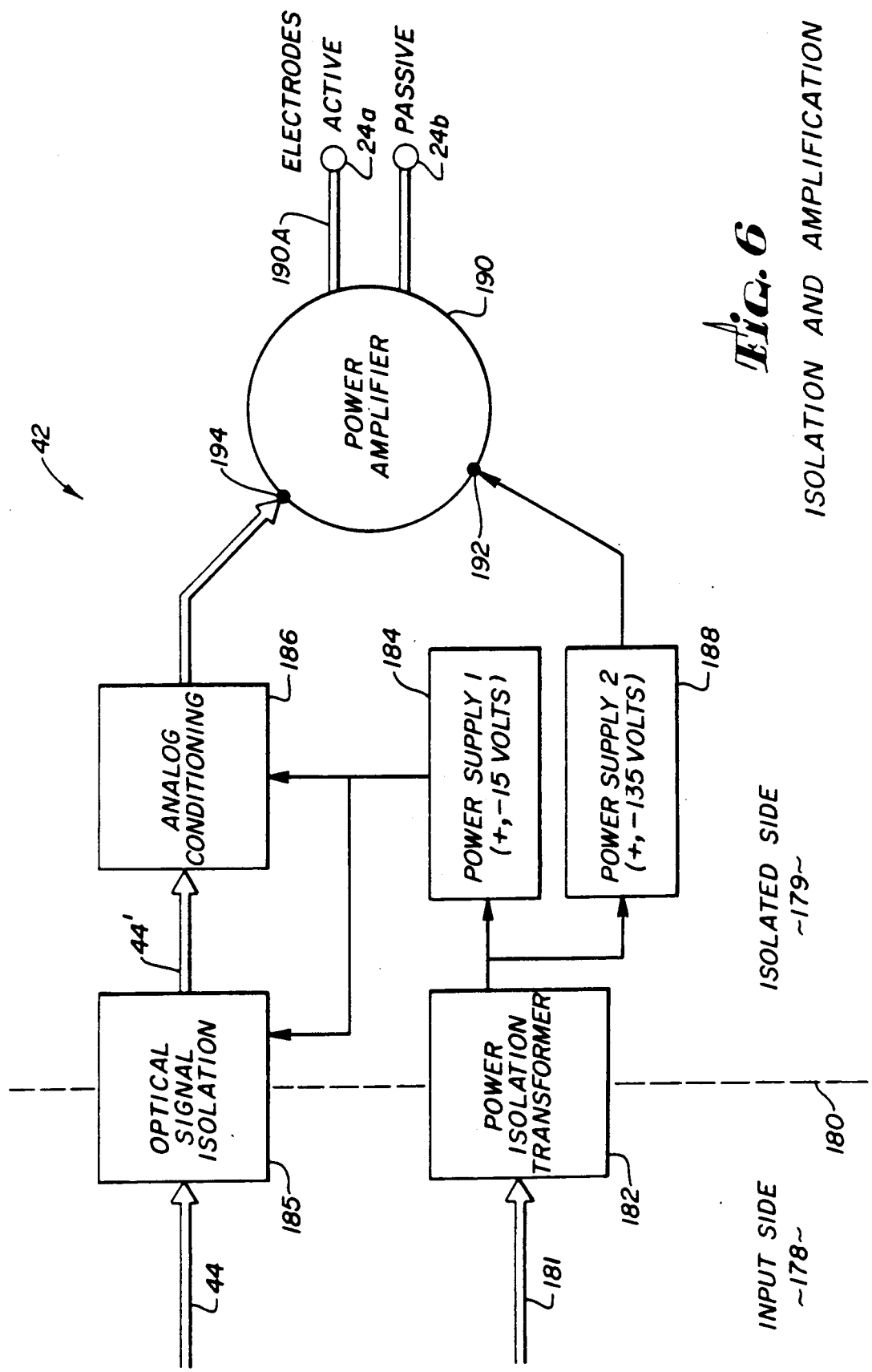
FIG. 6 is a functional block diagram of an isolation and amplification unit of the multichannel stimulator of FIG. 1.

FIG. 6 is a functional block diagram of an isolation and amplification unit 42 of the multichannel stimulator of FIG. 1. There is an input side 178 and an electrically isolated side 179. A conventional power isolation transformer receives AC input power 181 at its primary winding and produces an isolated power supply at its secondary winding. The power signal is rectified on the isolation side by power supplies 184 and 188 to produce DC power for the components on the isolation side and therefore distortion of the input AC power waveform is not of concern.

However, at 44 a carefully formed stimulus signal 60 is received at the input side 178 from a corresponding slave unit 40. Signal 44 is transferred without distortion to the isolated side 179 as signal 44' by means of an inexpensive ($2) TRW 6N135 optical signal isolator, basically an optical transmitter and receiver pair. Signal 44' is analog conditioned (such as removal of any bias needed to utilize the optical isolator 185) and then feed to a very linear power amplifier 190, such as an APEX PA08 (costing about $100), which can produce peak currents of about 100 ma. In practice it is found that the circuit of FIG. 6 can be produced for only about $150/unit. It has excellent electrical isolation at side 179 and the signal waveform of the output current 190A produced by amplifier 190 is a very high fidelity reproduction of the signal waveform of the stimulus input signal voltage 44 as the current ouptput 190A .

Figure 7:
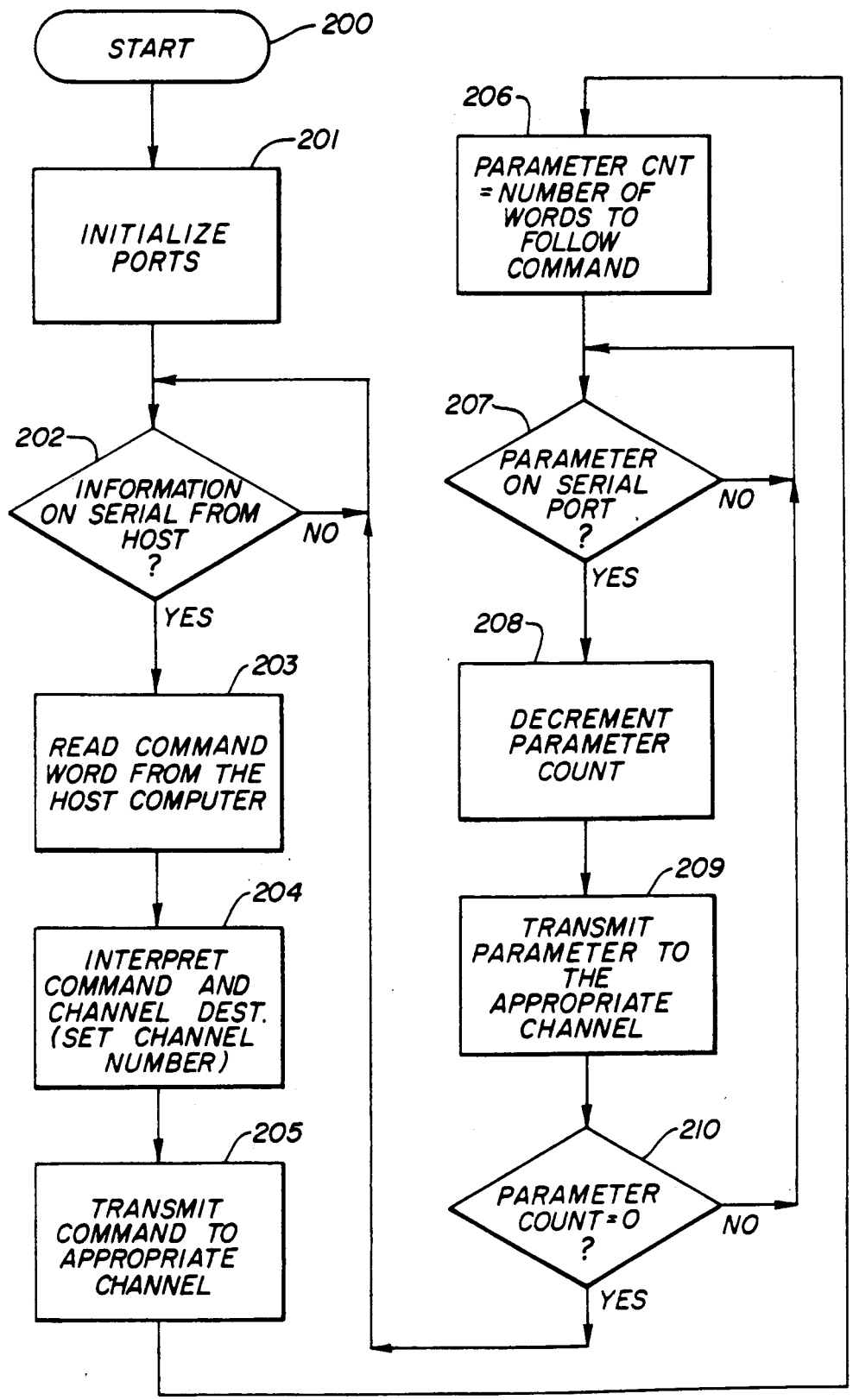
FIG. 7 is a flowchart of a computer program used to control the system master unit of FIG. 4.
Figure 9A:
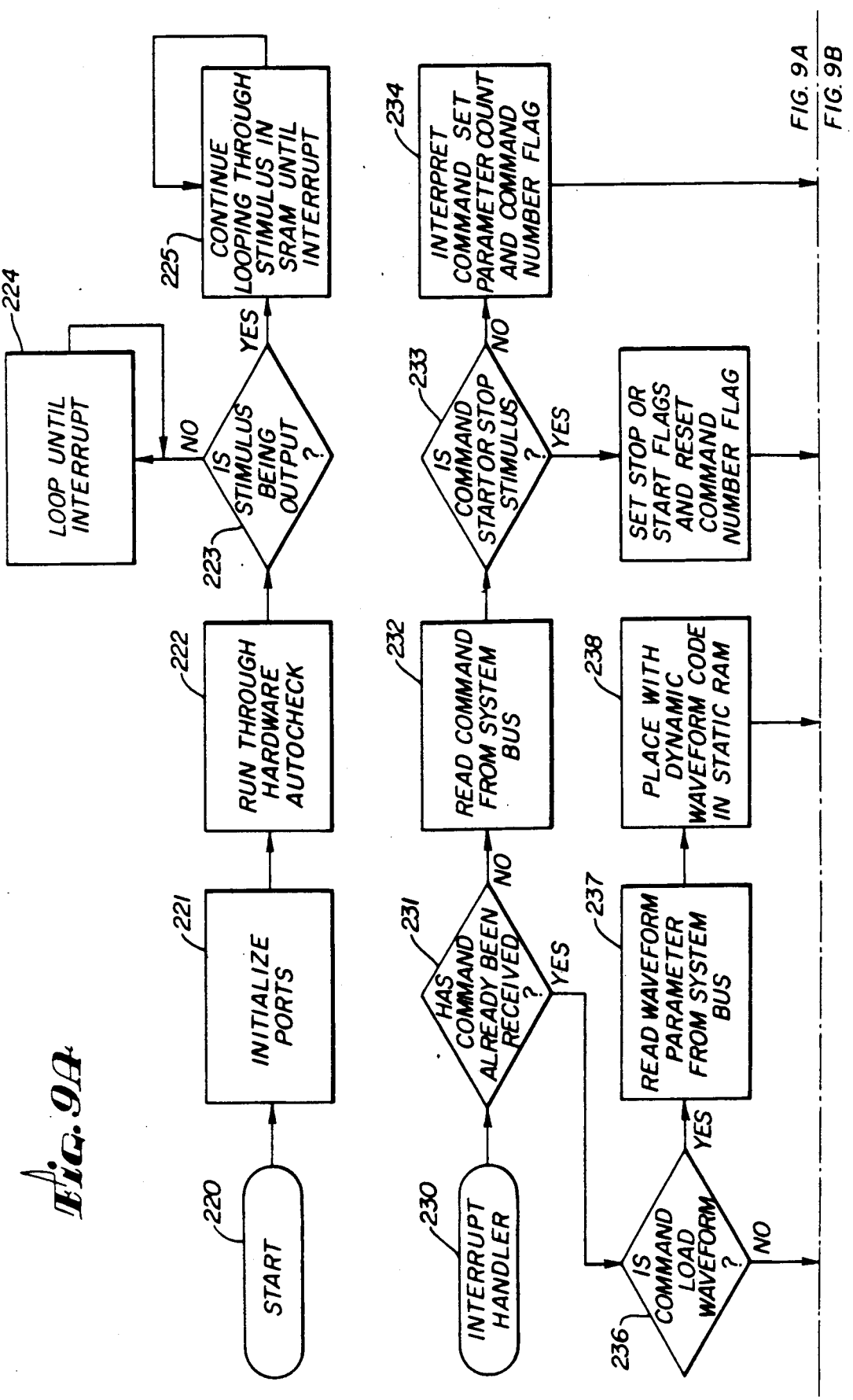
FIG. 9 is a flowchart of a computer program used to control one of the slave units of FIG. 5.

FIG. 7 is a flowchart of a computer program used to control the system master unit of FIG. 4 and FIG. 9 is a flowchart of a computer program used to control one of the slave units of FIG. 5.

Thus, there has been shown a novel multichannel stimulator enabling tuned stimulation with high fidelity stimulus waveforms controllable by means of a user-friendly interface. It is to be understood that various changes and modifications, and subsitutions in the form and details of the invention may be made by those skilled in the art without departing from the scope of the following claims.

APPENDIX 1

```
'*****************************************************
'****** Smart Stim - Host Software **************
'****    Oct. 15, 1988      *************************
'*****************************************************
'
' Software developed using Microsoft
' Basic for the Macintosh, Version 2.00
'
' Michael S. Morse
' (c)1988
'
DDL2%=150
VER$="2.02.14"
NCHAN=4:TLEN=200:GZERO=0:TCONS=10  '100COUNTS  IN 10 SEC
OPEN "COM1: 9600,N,8,1" AS #7
'OPEN "RAMDISK:SERIAL OUTPUT" FOR OUTPUT AS #7
DIM WNAME$(19),WAV%(19,50),TNAME$(19),TIM%(19,200)
DIM TIMES%(NCHAN),WAVES%(NCHAN),PARAM(NCHAN,5),WPARAM(19,5)
DIM WNUM%(NCHAN),TNUM%(NCHAN),ACT%(NCHAN),MAXPAR(5),PIC$(200)
DIM DPAR(5),FREQ%(160,2)  'Hz=1,count=2
WINDOW 1,"SmartStim "+VER$,,1
ON MENU GOSUB MEN
ON DIALOG GOSUB DIAL
ON MOUSE GOSUB MOUS
MENU 1,0,1,"File"
MENU 1,1,1,"New"
MENU 1,2,1,"Open"
MENU 1,3,1,"Save"
MENU 1,4,1,"Save As..."
MENU 1,5,1,"Quit"
MENU 1,6,1,"Import File"
BUTTON 5,1,"Start",(20,20)-(90,35),1
BUTTON 6,0,"Stop",(120,20)-(190,35),1
BUTTON 8,1,"Cyclic",(120,45)-(190,60),2
BUTTON 9,1,"Send",(220,20)-(280,35),1
MENU 2,0,0,"Waveform":MENU 3,0,0,"Timeform"
FOR X=1 TO 20
    MENU 2,X,1,"Wave "+STR$(X):MENU 3,X,1,"Time "+STR$(X)
NEXT X
MENU 6,0,1,"Windows"
MENU 6,1,1,"Wave definition"
MENU 6,2,1,"Simulation"
NCHAN=4
PI=3.141592654#
MAXPAR(1)=160:MAXPAR(2)=65535!:MAXPAR(3)=65535!:MAXPAR(4)=1:MAXPAR(5)=1
MINPAR(1)=1:MINPAR(2)=1:MINPAR(3)=0:MINPAR(4)=0:MINPAR(5)=0
DPAR(1)=1:DPAR(2)=1:DPAR(3)=100:DPAR(4)=.01:DPAR(5)=.01
GOSUB STOPALL
OPEN "FTABLE" FOR INPUT AS #10
N=1
WHILE EOF(10)<>-1
INPUT #10,FREQ%(N,1),FREQ%(N,2)
N=N+1
WEND
```

Walker-Auburn Stimulator Host Software
Michael S. Morse (c)1988

```
CLOSE #10
GOSUB WOPEN1
MENU ON
DIALOG ON
MOUSE ON
TIM0=TIMER
CHAN%=1
GOSUB DOMENUS
GOSUB DOBUTTONS
LOOPING:
S%=1:TIM0=TIMER
'*********************************************************
WHILE RUNIT=1
LOCATE 1,1
    FOR X%=1 TO NCHAN
        DATT=128-(TIM%(TNUM%(X%),S%)-128)*PARAM(X%,4)
        IF DATT>128-128*MTH THEN DATT=128-128*MTH
        PRINT #7,CHR$(X%*16+5)+CHR$(DATT);
            FOR DDL1%=1 TO DDL2%
            NEXT DDL1%
    NEXT
    IN$=INKEY$:IF IN$<>"" THEN GOSUB INR0
     IF S%<TLEN THEN S%=S%+1 ELSE GOSUB ENS
     FOR TDD=0 TO TDDY:NEXT TDD
 WEND
 IN$=INKEY$:IF IN$<>"" THEN GOSUB INR0
GOTO LOOPING
ENS:
IF CYCL=1 THEN S%=1 ELSE RUNIT=0:GOSUB SENDGZERO:GOSUB DOBUTTONS:GOSUB DOMENUS
RETURN
'*********************************************************
INR0:
DIALOG OFF
IF IN$=" " THEN GOSUB STOPALL :BEEP:BEEP:BEEP:BEEP:GOSUB   DOBUTTONS
IF IN$=CHR$(8) THEN GOSUB GOALL:BEEP
PAR%=VAL(IN$):IF PAR%>5 THEN DIALOG ON:RETURN
IF PAR%=0 AND IN$<>"0" THEN GOTO INR01
IF  PARAM(CHAN%,PAR%)<= MAXPAR(PAR%)-DPAR(PAR%) THEN
    PARAM(CHAN%,PAR%)=PARAM(CHA,PAR%)+DPAR(PAR%):SENDPARAM PAR%
DIALOG ON
RETURN
INR01:
PAR%=0
IF IN$="Q" OR IN$="q" THEN PAR%=1
IF IN$="W" OR IN$="w"THEN PAR%=2
IF IN$="E" OR IN$="e"THEN PAR%=3
IF IN$="R" OR IN$="r"THEN PAR%=4
IF IN$="T" OR IN$="t"THEN PAR%=5
IF  IN$="D" THEN   MOVETO  20,290
INPUT "COUNT IN SECS";TDDY$
TDDY=(VAL(TDDY$)-28)*TCONS
GOSUB DOPARAM
DIALOG ON
RETURN
```
Walker-Auburn Stimulator Host Software
Michael S. Morse (c)1988

```
IF IN$="M" THEN MOVETO  20,290
INPUT "MIN THRESHOLD:";MTH$
MTH=VAL(MTH$)-INT(VAL(MTH$))
GOSUB DOPARAM
DIALOG ON
RETURN
IF PAR%>0 AND PARAM(CHAN%,PAR%)>=MINPAR(PAR%)+DPAR(PAR%) THEN
   PARAM(CHAN%,PAR%)=PARAM(CHAN%,PAR%)-DPAR(PAR%)
IF IN$="P" OR IN$="p"THEN PAR%=15
ACT%(CHAN%)=0
```

```
GOSUB DOBUTTONS
IF PAR%>0 THEN SENDPARAM PAR%
DIALOG ON
RETURN

MOUS:
RETURN

MEN:
MENU OFF
DIALOG OFF
ON MENU(0) GOSUB M1,M2,M3,M4,M5,M6
MENU ON
DIALOG ON
MENU
RETURN

M1:
ON MENU(1) GOSUB NE,WOPEN1,WSAVE1,WSAVE,QUI,WOPEN
RETURN

QUI:
CLOSE
MENU RESET
END

M2:
WNUM%(CHAN%)=MENU(1)
GOSUB DOMENUS
GOSUB STOPALL
GOSUB DOBUTTONS
FOR XX%=1 TO 5
     PARAM(CHAN%,XX%)=WPARAM(WNUM%(CHAN%),XX%)
     SENDPARAM XX%
NEXT XX%
GOSUB SENDWAVE
GOSUB DRAWAVE
GOSUB GOALL
RETURN

M3:
TNUM%(CHAN%)=MENU(1)
GOSUB DOMENUS
GOSUB DRAWTIME
 Walker-Auburn Stimulator Host Software
 Michael S. Morse (c)1988

RETURN

M4:

M5:
RETURN

M6:
ON MENU(1) GOSUB M61,M62
RETURN

M61:
WINDOW 1
RUNIT=0
GOSUB SENDGZERO
GOSUB DRAWALL
RETURN

M62:
MENU 1,0,0
MENU 2,0,0
MENU 3,0,0
RUNIT=0
```

```
GOSUB STOPALL
GOSUB SENDGZERO
WINDOW 2,"Simulation",,1
M2=0
S=1
MENU ON
DIALOG ON
PENMODE 10
FOR S=1 TO TLEN
PICTURE ON
CIRCLE(127,15),13
LINE (120,30)-(140,50+63),,B 'PENSIZE 20,20
 MOVETO 120,30
  LINETO 120,30+63'
ANG1=PI/2-(PARAM(1,4)*TIM%(TNUM%(1),S)-GZERO)/GZERO*PI/2
IF ANG1>PI/2 THEN ANG1=PI/2 ELSE IF ANG1<0 THEN ANG1=0
ANG2=PI/2-COS(ANG1)*(PARAM(2,4)*TIM%(TNUM%(2),S)-GZERO)/GZERO*PI
IF ANG2>PI THEN ANG2=PI ELSE IF ANG2<ANG1 THEN ANG2=ANG1
P1X=51*COS(ANG1)
P1Y=51*SIN(ANG1)
P2X=47*COS(ANG2)
P2Y=47*SIN(ANG2)
ANG3=PI/2-(PARAM(3,4)*TIM%(TNUM%(3),S)-GZERO)/GZERO*PI/2
IF ANG3>PI/2 THEN ANG3=PI/2 ELSE IF ANG3<0 THEN ANG3=0
ANG4=PI/2-COS(ANG3)*(PARAM(4,4)*TIM%(TNUM%(4),S)-GZERO)/GZERO*PI
IF ANG4>PI THEN ANG4=PI ELSE IF ANG4<ANG3 THEN ANG4=ANG3
P3X=51*COS(ANG3)
P3Y=51*SIN(ANG3)
P4X=47*COS(ANG4)
P4Y=47*SIN(ANG4)
IF WINDOW(0)<>2 THEN RETURN
 Walker-Auburn Stimulator Host Software.
 Michael S. Morse (c)1988

MOVETO 120,30+63
PENSIZE 17,17
CALL LINE (P1X,P1Y)'17,17
PENSIZE 12,12
CALL LINE (P2X,P2Y)'12,12
MOVETO 120,30+63
PENSIZE 17,17
CALL LINE (P3X,P3Y)
PENSIZE 12,12
CALL LINE (P4X,P4Y)
PICTURE OFF
PIC$(S)=PICTURE$
NEXT S
S=1
CLS
WHILE WINDOW(0)=2
PICTURE ,PIC$(S)
PICTURE ,PIC$(S)
S=S+1
IF S>TLEN THEN S=1
WEND
MENU 1,0,1
MENU 2,0,1
MENU 3,0,1

RETURN

DIAL:
DIALOG OFF
ON DIALOG(0) GOSUB D1,D2,D3,D4,D5,RET
DIALOG ON
RET:
RETURN
```

```
D1:
BUTT=DIALOG(1)
IF BUTT<5 GOTO B5
IF BUTT=5 THEN RUNIT=1
GOSUB GOALL
MENU 3,0,0
MENU 2,0,0
IF BUTT=6 THEN RUNIT=0
GOSUB SENDGZERO
GOSUB DOMENUS
IF BUTT=8 THEN CYCL=ABS(CYCL-1)
IF BUTT=9 GOTO SENDALL
IF BUTT=10 GOTO B10
IF BUTT >10 AND BUTT <15 GOTO B11
GOSUB DOBUTTONS
RETURN

B5:
CHAN%=BUTT
GOSUB DOBUTTONS
 Walker-Auburn Stimulator Host Software
 Michael S. Morse (c)1988

GOSUB DOMENUS
RETURN

B10:
RETURN

B11:
CHAN%=BUTT-10
IF ACT%(CHAN%)=0 THEN ACT%(CHAN%)=1
SENDPARAM 0 ELSE ACT%(CHAN%)=0
  SENDPARAM &HF
GOSUB DOBUTTONS
GOSUB DOMENUS
RETURN

D2:
  RETURN

D3:
 WINDOW WINDOW(0)
 RETURN

D4:
IF WINDOW(4)=1 GOTO QUI ELSE WINDOW 1
RETURN

DOMENUS:
FOR XX=1 TO 19
    MENU 2,XX,1
    MENU 3,XX,1
NEXT XX
IF WNUM%(CHAN%)>0 THEN MENU 2,WNUM%(CHAN%),2
IF TNUM%(CHAN%)>0 THEN MENU 3,TNUM%(CHAN%),2
IF RUNIT=1 THEN  MENU 3,0,0
MENU 2,0,0 ELSE MENU 3,0,1
MENU 2,0,1
RETURN

D5:
IF WINDOW(0)=1 THEN GOSUB DRAWALL
RETURN

DOPARAM:
MOVETO 320,40
PRINT "DLY ";TDDY/10-28;"     TH  ";MTH
MOVETO 70,76
PRINT"  Hz       Cycles     Delay    %TForm    Amplitud"
```

```
FOR X=1 TO NCHAN
MOVETO 65,45+50*X
PRINT FREQ%(PARAM(X,1),1);
    FOR Y=2 TO 5
        MOVETO 10+Y*60,45+50*X
        PRINT PARAM(X,Y);
    NEXT Y
```

APPENDIX 2

```
;****************** MASTER SOFTWARE  ***************
; Michael S. Morse
; (c) 1988
; This software was developed in 8088 assembly language
; using a "UNIVERSAL CROSS ASSEMBLER - Version 2."

EPRA    EQU     0F800H
EPRB    EQU     0F801H
EPRAI   EQU     0F802H
EPRBI   EQU     0F803H
RAMI    EQU     00000H
RAMA    EQU     00001H
RAMB    EQU     00002H
RAMC    EQU     00003H
TIML    EQU     00004H
TIMH    EQU     00005H
TOPS    EQU     00042H
RAMINIT EQU     11000011B       ;AO BO CI
DATAIN          EQU     02000H
CONTROL         EQU     02100H
DATAOUT         EQU     RAMB
INTER EQU       RAMA
SEG7  EQU       EPRA

ORG     04000H
STROB:          DB      00H
        ORG     0000H
LEFTB:          DB      00H
LSB:    DB      00H
MSB:    DB      00H
CHAN:   DB      00H

ORG     0F800H
START:          MOV     DX,EPRAI        ;EAO
        MOV     AL,0FFH
        OUT     DX,AL
        MOV     DX,EPRBI        ;EBO
        OUT     DX,AL
        MOV     DX,TIML
        MOV     AL,04H          ;9600 BAUD
        OUT     DX,AL
        MOV     DX,TIMH
        MOV     AL,040H         ;SQR WAVE
        OUT     DX,AL
        MOV     DX,RAMI         ;R CW
        MOV     AL,RAMINIT
        OUT     DX,AL
        LEA     DX,INTERR
        MOV     WORD PTR 08H,DX ;NMI ROUTINE
        MOV     WORD PTR 0AH,0000H
        MOV     SP,TOPS
        MOV     BP,0    ;START CLEAN
        MOV     DX,CONTROL              ;PROGRAM SERIAL PORT
```

Walker-Auburn Stimulation System - Master Software
Michael S. Morse (c)1988

```
        MOV     AL,01001111B
        OUT     DX,AL
        MOV     AL,00010101B
        OUT     DX,AL
        MOV     DX,SEG7
        LEA     BX,HELLO
        CALL    MESSAG
        XOR     AL,AL
        MOV     CHAN,0
        MOV     BX,0
LOOO:   MOV     AL,CHAN
        CALL    OUT7SEG
        MOV     AL,0FH                  ;STOP ALL CHANELS
        CALL    SEND
        MOV     CX,08FFH
DELO:   LOOP    DELO
        CMP     BYTE PTR CHAN,0FH
        INC     BYTE PTR CHAN
        JNE     LOOO
        LEA     BX,ENDTST
        CALL    MESSAG
        MOV     AL,10111001B            ;'o'
        CALL    OUT7SEG

;BP = TYPE
                                ;AL = DATA
                                ;CX = COUNTER
;************************************************************
;       MAIN LOOP
;************************************************************

LOO:
        LEA     BX,HELLO
        CALL    MESSAG
        JMP     LOO
;************************************************************
RUNING:     MOV     AL,CHAN
OUT7SEG:    MOV     DX,SEG7
            OUT     DX,AL
            RET

SEND:   MOV     DX,DATAOUT
        OUT     DX,AL                   ;DATA TO SLAVE
        MOV     DX,INTER
        MOV     AL,CHAN                 ;CHANNEL NUMB
        OUT     DX,AL
        MOV     STROB,AL                ;STROBIT
        RET

GOIN:   CALL    RUNING
GO:     MOV     DX,DATAIN
        MOV     AL,0FFH
        OUT     DX,AL
        IRET
```

Walker-Auburn Stimulation System - Master Software
Michael S. Morse (c)1988

```
MESSAG:     MOV     DX,DATAIN
        MOV     AL,BYTE PTR [BX]
        JZ      MESEND
        OUT     DX,AL
        INC     BX
        MOV     CX,01FH
MDEL:   LOOP    MDEL
        JMP     MESSAG
```

```
MESEND:         RET

HELLO:          DB      'Waveform sintetizer'
        DB      13,10
        DB      '   Andrew Cilia  1988'
        DB      0
ENDTST:         DB      'AUTO. TEST FINISHED. All systems up.'
        DB      0

INTERR:         MOV     DX,DATAIN               ;GET DATA FROM BUS
        IN      AL,DX
        OUT     DX,AL                   ;ECHO
        CMP     BP,0
        JE      SETYPE
        CMP     BP,01H
        JNE     IN2
        JMP     SETFRE
IN2:    CMP     BP,02H
        JNE     IN3
        JMP     SETBUR
IN3:    CMP     BP,03H
        JNE     IN4
        JMP     SETDEL
IN4:    CMP     BP,04H
        JNE     IN5
        JMP     LOADWA
IN5:    CMP     BP,05H          ;GAIN
        JNE     IN6
        CALL    SEND
        MOV     BP,0
        JMP     GO
IN6:
IN7:    CMP     BP,07H
        JNE     IN8
        CALL    SEND
        MOV     BP,0
        JMP     GO
IN8:    CMP     BP,08H
        JNE     IN9
        CALL    SEND
        MOV     BP,0
        JMP     GO
IN9:
INA:
INB:
```

Walker-Auburn Stimulation System - Master Software
Michael S. Morse (c)1988

```
INC:
IND:
INE:
IBACK:          MOV     BP,0            ; HELP MY SOUL!! AN ERROR!!!!
        MOV     LEFTB,0
        MOV     AL,0FH          ;STOP THE CHANNEL
        CALL    SEND
        MOV     AL,11110011B    ;'E'
        CALL    OUT7SEG
        JMP     GO

SETYPE:         MOV     CHAN,AL         ;GET CHANNEL #
        AND     CHAN,0F0H
        MOV     CL,3
        SHR     CHAN,CL
        AND     AL,0FH          ;CLEAN COMMAND NIBBLE
        CMP     AL,0FH          ;STOP!!
        JNE     ST1
        CALL    SEND
        MOV     AL,10111001B    ;'o'
        CALL    OUT7SEG
        JMP     GO
```

```
ST1:    CMP     AL,00H
        JNE     ST11
        CALL    SEND            ;CONTINUE
        JMP     GOIN

ST11:   MOV     BP,AX           ;START ROUTINES
        AND     BP,0FH          ;MASK OFF AH
        CMP     AL,01           ;FREC
        JNE     ST2
        CALL    SEND
        MOV     LEFTB,2
        MOV     AL,00001100B    ;'1'
        CALL    OUT7SEG
        JMP     GO
ST2:    CMP     AL,02           ;BURST
        JNE     ST3
        CALL    SEND
        MOV     LEFTB,2
        MOV     AL,10110111B    ;'2'
        CALL    OUT7SEG
        JMP     GO
ST3:    CMP     AL,03           ;INTER BURST DELAY
        JNE     ST4
        CALL    SEND
        MOV     LEFTB,2
        MOV     AL,10011111B    ;'3'
        CALL    OUT7SEG
        JMP     GO
ST4:    CMP     AL,04           ;WAVE DATA
        JNE     ST5
        CALL    SEND
        MOV     LEFTB,49
```

Walker-Auburn Stimulation System - Master Software
Michael S. Morse (c)1988

```
        MOV     AL,11001101B    ;'4'
        CALL    OUT7SEG
        JMP     GO
ST5:    CMP     AL,05           ;GAIN
        JNE     ST6
        CALL    SEND
        MOV     LEFTB,1
        MOV     AL,11011011B    ;'5'
        CALL    OUT7SEG
        JMP     GO
ST6:    CMP     AL,06
        JNE     ST7
        MOV     LEFTB,1
        MOV     AL,11111001B    ;'6'
        CALL    OUT7SEG
        JMP     GO
ST7:    CMP     AL,07
        JNE     ST8
        MOV     LEFTB,1
        CALL    SEND
        MOV     AL,00001110B    ;'7'
        CALL    OUT7SEG
        JMP     GO
ST8:    CMP     AL,08
        JNE     ST9
        MOV     LEFTB,1
        CALL    SEND
        MOV     AL,11111111B    ;'8'
        CALL    OUT7SEG
        JMP     GO
ST9:    JMP     GO
```

```
SETFRE:      CMP       LEFTB,2
             JNE       SF0
             CALL      SEND
             DEC       LEFTB
             JMP       GO
SF0:         CALL      SEND
             MOV       LEFTB,0
             MOV       BP,0
             JMP       GOIN

SETBUR:      CMP       LEFTB,2
             JNE       SB0
             CALL      SEND
             DEC       LEFTB
             JMP       GO
SB0:         CALL      SEND
             DEC       LEFTB
             MOV       BP,0
             JMP       GOIN

SETDEL:      CMP       LEFTB,2
             JNE       SD0
```

Walker-Auburn Stimulation System - Master Software
Michael S. Morse (c)1988

```
             CALL      SEND
             DEC       LEFTB
             JMP       GO
SD0:         CALL      SEND
             DEC       LEFTB
             MOV       BP,0
             JMP       GOIN

LOADWA:      CALL      SEND
             DEC       LEFTB
             JNZ       LW0              ;FINISH?
             MOV       BP,0             ;YEA
             JMP       GOIN
LW0:         MOV       AL,LEFTB         ;DISPLAY COUNT
             CALL      OUT7SEG
             JMP       GO

ORG       0FFF0H           ;RESET ADDRESS
             JMP       START

END
```

APPENDIX 3

```
;************************BOARD SLAVE AUTOTEST SOFTWARE ************************
;********************************* 10/14/88    ********************************
;********************************* V 1.3 **************************************
;
; Michael S. Morse (c)1988
;
; This software was developed in 8088 assembly language
; using a "UNIVERSAL CROSS ASSEMBLER - Version 2."

EPRA    EQU     0F800H
        EPRB    EQU     0F801H
        EPRAI   EQU     0F802H
        EPRBI   EQU     0F803H
        RAMI    EQU     00000H
        RAMA    EQU     00001H
        RAMB    EQU     00002H
        RAMC    EQU     00003H
        TIML    EQU     00004H
        TIMH    EQU     00005H
        TOPS    EQU     00042H
        RAMINIT EQU     11000001B       ;A0 BI CI
        DA      EQU     EPRA
        GAIN    EQU     EPRB
        DATAIN          EQU     RAMB
        SEG7    EQU     RAMA
        ZERO    EQU     080H
        GZERO   EQU     080H

ORG     00000H
LEFTB:          DB      00H
WAITFL:         DB      00H
LSB:    DB      00H
MSB:    DB      00H
MGAIN:          DB      00H

ORG     0800FH
PROG:   RET

ORG     0F800H
START:          LEA     DX,INTERR
        MOV     WORD PTR 08H,DX
        MOV     WORD PTR 0AH,0000H
        MOV     SP,TOPS
        MOV     DX,DA
        MOV     AL,ZERO
        OUT     DX,AL
        MOV     DX,GAIN
        MOV     AL,GZERO
        OUT     DX,AL
        MOV     DX,EPRAI        ;EAO
        MOV     AL,0FFH
        OUT     DX,AL
        MOV     DX,EPRBI        ;EBO
        OUT     DX,AL
        MOV     DX,TIML         ;START TIMER FAST.
        MOV     AL,04H
        OUT     DX,AL
        MOV     DX,TIMH
        MOV     AL,0C0H
        OUT     DX,AL
        MOV     DX,RAMI         ;R CW
        MOV     AL,RAMINIT
        OUT     DX,AL
```

```
        MOV     MGAIN,GZERO
        MOV     BP,0        ;START CLEAN
        LEA     DI,PROG
        MOV     BX,00H                      ;NO DELAY INTERBURST
        MOV     SI,00H                      ;MAX BURST LENGTH
        MOV     BYTE PTR [DI],0C3H          ;SET RET AT PROG
        MOV     WAITFL,0FFH
        CALL    RUNING
        MOV     AH,00001110B                ;STOP AND LOADW STOP

;DX = DA CONV ADDR
                                ;BP = TYPE
                                ;BX = DELAY
                                ;SI = BURST LENGTH
                                ;AH = STOP FLAG
                                ;BIT    1= 0 GAIN
                                ;       2= WAVE LOAD
                                ;       3= STOP COMM
                                ;       4= AUTOTESTING
                                ;AL = DATA
                                ;CX = COUNTER
;*********************************************************
;       MAIN LOOP
;*********************************************************
        MOV     DX,DA
LO0:    CMP     AH,00       ;STOP?
        JNE     WAITIN      ;DONT RUN
        MOV     CX,SI
LO1:    CALL    PROG        ;BURST
RETP:   LOOP    LO1
        CMP     BX,00
        JE      LO0         ;NO DELAY
        MOV     CX,BX       ;DELAY INTER BURST
        MOV     AL,ZERO     ;TURN IT OFF
        OUT     DX,AL
LO2:    LOOP    LO2
        JMP     LO0

WAITIN: CALL    RUNING
W0:     CMP     AH,00
        JNE     W0
        CALL    RUNING
        JMP     LO0

;*********************************************************
RUNING:     MOV     AL,10000001B    ;'r'
        CMP     AH,00
        JE      OUT7SEG
        MOV     AL,10111001B    ;'o'
OUT7SEG: MOV    DX,SEG7
        OUT     DX,AL
        RET

GOIN:   CALL    RUNING
GO:     AND     DX,00FFH    ;GET OLD
        AND     AX,0FF00H   ;KEEP NEW
        OR      AX,DX
        MOV     DX,DA
        POPF
        IRET

INTERR:     PUSHF
        MOV     DX,DATAIN           ;GET DATA FROM BUS
        IN      AL,DX
        CMP     BP,0
        JE      SETYPE
;_____
        CMP     BP,05H              ;GAIN
        JNE     IN1
        MOV     DX,GAIN
        OUT     DX,AL
```

```
        MOV     BYTE PTR MGAIN,AL
        MOV     BP,0
        CALL    OUT7SEG
        AND     AH,11111101B        ;TEST FOR ZERO GAIN
        CMP     AL,GZERO            ;ZERO GAIN
        JNE     GO
        OR      AH,00000010B        ;STOP WAVE FOR 0 GAIN (BIT1=1)
        MOV     CX,1
        JMP     GO
;_____
IN1:    CMP     BP,01H
        JNE     IN2
        JMP     SETFRE
IN2:    CMP     BP,02H
        JNE     IN3
        JMP     SETBUR
IN3:    CMP     BP,03H
        JNE     IN4
        JMP     SETDEL
IN4:    CMP     BP,04H
        JNE     IN5
        JMP     LOADWA
IN5:
IN6:    CMP     BP,06H              ;RESET
        JNE     IN7
        JMP     START
I-7:    CMP     BP,07H
        JNE     IN8
        JMP     AUTOTES
IN8:    CMP     BP,08H
        JNE     IN9
IN9:
IBACK:  MOV     BP,0                ;O MY GOSH! AN ERROR!
        MOV     LEFTB,0
        MOV     CX,01H              ;STOP BURST
        MOV     AH,08H              ;STOP IT
        MOV     AL,11110011B        ;'E'
        CALL    OUT7SEG
        JMP     GO

;SETGA:  MOV    DX,GAIN             ;GAIN UPDATE
;       OUT     DX,AL               ;RANGE 0-FF =-1 TO 1
;       MOV     BP,0
;       MOV     BYTE PTR MGAIN,AL
;       JMP     GOIN

SETYPE: CMP     AL,0FH              ;STOP!!
        JNE     ST1
        OR      AH,00001000B        ;STOP RUN (BIT3=1)
        MOV     CX,01
        JMP     GOIN
ST1:    CMP     AL,00H
        JNE     ST11
        AND     AH,11110111B        ;OVERWRITE STOP
        MOV     CX,01
        JMP     GOIN
;---------------------COMMANDS---------------------
ST11:   MOV     BP,AX
        AND     BP,0FH              ;MASK OFF AH
        CMP     AL,01               ;FREC
        JNE     ST2
        MOV     LEFTB,2
        MOV     AL,00001100B        ;'1'
        CALL    OUT7SEG
        JMP     GO
ST2:    CMP     AL,02               ;BURST
        JNE     ST3
        MOV     LEFTB,2
        MOV     AL,10110111B        ;'2'
        CALL    OUT7SEG
        JMP     GO
```

```
ST3:    CMP     AL,03               ;INTER BURST DELAY
        JNE     ST4
        MOV     LEFTB,2
        MOV     AL,10011111B        ;'3'
        CALL    OUT7SEG
        JMP     GO
ST4:    CMP     AL,04               ;WAVE DATA
        JNE     ST5
        LEA     DI,PROG
        MOV     LEFTB,49
        MOV     AL,11001101B        ;'4'
        CALL    OUT7SEG
        MOV     CX,01H              ;STOP BURST
        OR      AH,00000100B        ;STOP FOR WAVE LOAD (BIT2=1)
        JMP     GO
ST5:    CMP     AL,05               ;GAIN
        JNE     ST6
        MOV     LEFTB,1
        MOV     AL,11011011B        ;'5'
        CALL    OUT7SEG
        JMP     GO
ST6:    CMP     AL,06
        JNE     ST7
ST7:    CMP     AL,07
        JNE     ST8
        MOV     AL,00001110B        ;'7'
        CALL    OUT7SEG
        JMP     GO
ST8:    JMP     GO

SETFRE:         CMP     LEFTB,2
        JNE     SF0
        MOV     DX,TIML
        OUT     DX,AL
        MOV     WAITFL,AL                   ;SET WAIT FLAG
        DEC     LEFTB
        JMP     GO
SF0:    MOV     DX,TIMH             ;SET TIMODE
        OR      WAITFL,AL           ;SET WAIT FLAG
;       CMP     WAITFL,02H
;       JA      SPFREQ
;       MOV     DX,TIML
;       MOV     AL,2                ;NO VALUES BELOW 2 TO TIMER
;       OUT     DX,AL
;       MOV     DX,TIMH
;       MOV     AL,0C0H
SPFREQ:         OR      AL,0C0H             ;PULSE
        OUT     DX,AL
        MOV     DX,RAMI             ;START TIMER
        MOV     AL,RAMINIT
        OUT     DX,AL
        MOV     LEFTB,0
        MOV     BP,0
        JMP     GOIN

SETBUR: CMP     LEFTB,2
        JNE     SB0
        MOV     LSB,AL
        DEC     LEFTB
        JMP     GO
SB0:    MOV     MSB,AL
        MOV     SI,WORD PTR LSB     ;SI = BURST LENGTH
        MOV     LEFTB,0
        MOV     BP,0
        JMP     GOIN

SETDEL:         CMP     LEFTB,2
        JNE     SD0
        MOV     LSB,AL
        DEC     LEFTB
        JMP     GO
```

```
SD0:    MOV     MSB,AL
        MOV     BX,WORD PTR LSB
        MOV     LEFTB,0
        MOV     BP,0
        JMP     GOIN

LOADWA:     MOV     BYTE PTR [DI],0B0H      ;MOV AL, (OVERWRITE LAST RET)
        INC     DI
        MOV     BYTE PTR [DI],AL            ;#H
        INC     DI
        MOV     BYTE PTR [DI],0EEH          ;OUT DX,AL
        INC     DI
        CMP     BYTE PTR WAITFL,0
        JE      NOWAIT
        MOV     BYTE PTR [DI],09BH          ;WAIT
        INC     DI
NOWAIT:     MOV     BYTE PTR [DI],0C3H      ;RET
        DEC     LEFTB
        JNZ     LW0                         ;FINISH?
        MOV     BP,0                        ;YEA
        AND     AH,11111011B                ;OUT WAVE STOP
        JMP     GOIN
LW0:    MOV     AL,LEFTB                    ;DISPLAY COUNT
        CALL    OUT7SEG
        JMP     GO

AUTOTES:
        MOV     BP,0
        MOV     AH,0
        MOV     AH,00001000B
        MOV     AL,11101111B                ;'A'
        CALL    OUT7SEG
AT1:    CMP     BP,0
        JNE     GOIN2
        CMP     AH,0
        JNE     GOIN2
        CALL    PROG                        ;BURST
        INC     CL                          ;GAIN RAMP
        MOV     AL,CL
        MOV     DX,GAIN
        OUT     DX,AL
        MOV     DX,DA
        JMP     AT1
GOIN2:      MOV     DX,DA
        MOV     AH,0FH
        POPF
        IRET

NEXT X
RETURN

DOBUTTONS:
FOR BB=1 TO NCHAN
    IF ACT%(BB)=0 THEN BUTTON BB+10,1 ELSE BUTTON BB+10,2
    IF BB=CHAN% THEN BUTTON BB,2 ELSE BUTTON BB,1
NEXT BB
IF RUNIT=1 THEN BUTTON 5,0
BUTTON 6,1
BUTTON 9,0 ELSE BUTTON 5,1
BUTTON 6,0
BUTTON 9,1
IF CYCL=1 THEN BUTTON 8,2 ELSE BUTTON 8,1
RETURN

SUB SENDPARAM (PAR%) STATIC
SHARED PARAM(),CHAN%,FREQ%()
        IF PAR%=1 THEN MOVETO 65,45+50*CHAN%
        PRINT FREQ%(PARAM(CHAN%,1),1)
        IF PAR%>1 AND PAR%<15 THEN PA=PARAM(CHAN%,PAR%)
        MOVETO 8+PAR%*60,45+50*CHAN%
        PRINT PA;
        IF PAR%=4 GOTO ENS1
```

```
        MOVETO 20,290
        PRINT CHAN%;" ";PAR%;"  ";
            PRINT #7,CHR$(CHAN%*16+PAR%);
                FOR DDL1%=1 TO DDL2%
                NEXT DDL1%
            IF PAR%=0 OR PAR%=15 THEN GOTO ENS1
            IF PAR%=1 THEN PA=FREQ%(PARAM(CHAN%,1),2)
            IF PAR%=5 THEN PA=128-INT(PA*128)
    PRINT PA-INT(PA / &HFF)*&HFF;" ";
            PRINT #7,CHR$(PA-INT(PA / &HFF)*&HFF);
                FOR DDL1%=1 TO DDL2%
                NEXT DDL1%
            IF  PAR%<4 THEN PRINT #7,CHR$(INT(PA/&HFF));
            PRINT INT(PA/&HFF)
              .   FOR DDL1%=1 TO DDL2%
                NEXT DDL1%
ENS1:END SUB

STOPALL:
XX=CHAN%
FOR CHAN%=1 TO NCHAN
    PARAM(CHAN%,5)=GZERO
    SENDPARAM 5
    SENDPARAM 15
    ACT%(CHAN%)=0
NEXT
CHAN%=XX
IF RUNIT=1 THEN RUNIT=0
GOSUB DOBUTTONS
GOSUB DOMENUS
RETURN

GOALL:
XX=CHAN%
FOR CHAN%=1 TO NCHAN
    IF ACT%(CHAN%)=0 THEN SENDPARAM 15 ELSE SENDPARAM 0
    BUTTON CHAN%+10,1
.NEXT
CHAN%=XX
RETURN

SENDGZERO:
FOR XX=1 TO NCHAN
    PARAM(XX,5)=GZERO
NEXT XX
                    'DON'T PUT A RETURN !!
SEND5:
XX=CHAN%
FOR CHAN%=1 TO NCHAN
     SENDPARAM 5
NEXT
CHAN%=XX
RETURN

SENDALL:
XYY%=CHAN%
FOR CHAN%=1 TO NCHAN
    GOSUB SENDWAVE
NEXT CHAN%
CHAN%=XYY%

SENDWAVE:
        FOR XX%=1 TO 5
            SENDPARAM  XX%
        NEXT XX%
        PRINT #7,CHR$(CHAN%*16+4);
            FOR DDL1%=1 TO DDL2%
            NEXT DDL1%
        FOR XX%=1 TO 50
            PRINT #7,CHR$(WAV%(WNUM%(CHAN%),XX%));
            FOR DDL1%=1 TO DDL2%
            NEXT DDL1%
```

```
        MOVETO 20,290
        PRINT WAV%(WNUM%(CHAN%),XX%)
            NEXT XX%
RETURN

DRAWALL:
XXY%=CHAN%
CLS
GOSUB DOPARAM
FOR CHAN%=1 TO NCHAN
    GOSUB DRAWAVE
    GOSUB DRAWTIME
NEXT
CHAN%=XXY%
RETURN

DRAWAVE:
PENSIZE 2,2
LINE (400,(CHAN%-1)*50+100)-STEP(50,-50),30,BF
LINE (400,(CHAN%-1)*50+100)-STEP(50,-50),,B
LINE (400,(CHAN%-1)*50+75)-STEP(50,0)
MOVETO 400,(CHAN%-1)*50+100-WAV%(WNUM%(CHAN%),1)*50/256
FOR XX%=1 TO 50
    LINETO 400+XX%,(CHAN%-1)*50+100-WAV%(WNUM%(CHAN%),XX%)*50/256
NEXT XX%
PENSIZE 2,2
RETURN

DRAWTIME:
PENSIZE 2,2
LINE (20,CHAN%*50+50)-STEP(350,20),30,BF
LINE (20,CHAN%*50+50)-STEP(350,20),,B
LINE (20,CHAN%*50+60)-STEP(350,0)
MOVETO 20,CHAN%*50+70-TIM%(TNUM%(CHAN%),1)*20/256
FOR XX%=1 TO TLEN
LINETO 20+XX%*350/TLEN,CHAN%*50+70-TIM%(TNUM%(CHAN%),XX%)*20/256
NEXT XX%
PENSIZE 2,2
RETURN

WOPEN1: FIL$=FILES$(1,"TEXT")
IF FIL$="" THEN BEEP
GOTO NE
GOTO WOPEN2
WOPEN:
FIL$=FILES$(1,"TEXT")
IF FIL$="" THEN BEEP
RETURN
OPEN FIL$ FOR INPUT AS #8
FIL$=FILES$(0,"Save Waveform as..")
IF FIL$="" THEN BEEP
RETURN
OPEN FIL$ FOR OUTPUT AS #10
FOR X=1 TO LOF(8)
    FD$=INPUT$(1,#8)
    IF FD$=CHR$(9) THEN  FD$=","
    PRINT #10,FD$;
NEXT X
CLOSE #8,#10
WOPEN2:
OPEN FIL$ FOR INPUT AS #8
INPUT #8,A$
IF A$<>VER$ THEN BEEP
BEEP
CLOSE #8
GOTO  WOPEN1
```

```
INPUT #8,NWAVE,NTIME,TLEN
'ERASE WNAME$,WAV%,TNAME$,TIM%,TIMES%,WAVES%,WPARAM,PARAM
'ERASE WNUM%,TNUM%,PIC$

'DIM TIMES%(NCHAN),WAVES%(NCHAN),PARAM(NCHAN,5),WPARAM(19,5)
'DIM WNUM%(NCHAN),TNUM%(NCHAN),PIC$(200)
FOR X=1 TO NCHAN
    INPUT#8,WNUM%(X),TNUM%(X)
      FOR Y=1 TO 4
          INPUT#8,PARAM(X,Y)
      NEXT Y
      PARAM(X,5)=GZERO
NEXT X
FOR X=1 TO 19
    INPUT#8,WNAME$(X)
    MENU 2,x,1,WNAME$(X)
    FOR Y=1 TO 5
        INPUT#8,WPARAM(X,Y)
    NEXT Y
    FOR Y=1 TO 50
        INPUT #8,WAV%(X,Y)
         IF WAV%(X,Y)>255 THEN WAV%(X,Y)=255
     NEXT Y
 NEXT X
FOR X=1 TO 19
    INPUT #8,TNAME$(X)
    MENU 3,x,1,TNAME$(X)
    FOR Y=1 TO TLEN
        INPUT #8,TIM%(X,Y)
     NEXT Y
 NEXT X
 FOR X=1 TO NCHAN:ACT%(X)=0:NEXT X
 'GOSUB DOMENUS:GOSUB DOBUTTONS
CLOSE #8
NE:
WINDOW 1
CLS
FOR X=1 TO NCHAN
    BUTTON X,1,"#"+HEX$(X), (5,30+50*X)-(50,45+50*X),2
    BUTTON X+10,1,"", (5,50+50*X)-(50,65+50*X),3
      CHAN%=X:GOSUB SENDWAVE
NEXT X
GOSUB DRAWALL
GOSUB DOBUTTONS:GOSUB DOMENUS
MENU 2,0,1:MENU 3,0,1:CHAN%=1
RETURN

WSAVE:
FILENAME$=FILES$(0,"Save waveforms as..")
IF FILENAME$="" THEN RETURN
FIL$=FILENAME$
WSAVE1:
IF FIL$="" THEN WSAVE
OPEN FIL$ FOR OUTPUT AS #8
PRINT#8,VER$
PRINT #8,NWAVE,NTIME,TLEN
BUTTON 5,1,"Start",(20,20)-(90,35),1
BUTTON 6,0,"Stop",(120,20)-(190,35),1
FOR X=1 TO NCHAN
    PRINT#8,WNUM%(X);",";TNUM%(X);",";
      FOR Y=1 TO 4
        IF Y<5 THEN  PRINT #8,PARAM(X,Y);","; ELSE PRINT #8,PARAM(X,Y)
    NEXT Y
NEXT X
FOR X=1 TO 19
    PRINT #8,WNAME$(X)
      FOR Y=1 TO 5
        IF Y<5 THEN  PRINT #8,WPARAM(X,Y);","; ELSE PRINT #8,WPARAM(X,Y)
    NEXT Y
    FOR Y=1 TO 50
        IF Y<50 THEN PRINT #8,WAV%(X,Y);","; ELSE PRINT #8,WAV%(X,Y)
```

```
         NEXT Y
      NEXT X
      FOR X=1 TO 19
           PRINT #8,TNAME$(X)
           FOR Y=1 TO 200
                IF Y<200 THEN PRINT #8,TIM%(X,Y);","; ELSE PRINT #8,TIM%(X,Y)
           NEXT Y
      NEXT X
      CLOSE #8
      GOSUB DRAWALL
      RETURN
```

I claim:

1. A multichannel stimulator apparatus having a plurality of channels, the apparatus comprising:
   (a) host user interface means for enabling a user to select a channel from the plurality of channels, to create and display a stimulus wave signal for the selected channel and to generate a data signal specifying the channel and stimulus wave signal;
   (b) master means for receiving the data signal and directing it to the specified channel as a wave building instruction signal;
   (c) slave unit means associated with the channel specified and responsive to the wave building signal to generate a corresponding low power stimulus wave signal in the channel specified, said slave unit means including logic circuitry; and
   (d) means coupled to the slave unit means for electrically isolating the low power stimulus wave signal from other channels and amplifying and converting it to a corresponding high fidelity current stimulus wave signal.

2. Apparatus as claimed in claim 1, further comprising a plurality of slave unit means, each slave unit means being associated with a respective channel.

3. Apparatus as claimed in claim 1, wherein the means for electrically isolating comprises an optical signal isolator for receiving the low power stimulus wave signal and for providing an isolated signal therefrom.

4. Apparatus as claimed in claim 3, wherein the optical signal isolator comprises an optical transmitter and receiver pair.

5. Apparatus as claimed in claim 1, wherein the host user interface means comprises means for producing graphically complex waveforms.

6. A multichannel stimulator apparatus having a plurality of channels, the apparatus comprising:
   channel selecting means for selecting a channel from the plurality of channels;
   signal selecting means for selecting an electrical signal having desired signal characteristics and for providing a data signal corresponding to the signal characteristics of the selected electrical signal;
   control means for directing the data signal to the selected channel as a wave building instruction signal; and
   a plurality of slave units corresponding in number to the plurality of channels, the plurality of slave units being simultaneously associated with the plurality of channels such that each slave unit is associated with a respective channel, each slave unit having logic circuitry and a stimulus signal providing means responsive to the wave building instruction signal directed to the respective channel to which the slave unit is connected for providing a stimulus wave signal.

7. Apparatus as claimed in claim 6, further comprising means connected to each slave unit to electrically isolate the stimulus wave signal provided by the slave unit from other channels and or amplifying and converting the stimulus wave signal to a corresponding high fidelity current stimulus wave signal.

8. Apparatus as claimed in claim 7, wherein the means for electrically isolating comprises an optical signal isolator for receiving the stimulus wave signal and for providing an isolated signal therefrom.

9. Apparatus as claimed in claim 8, wherein the optical signal isolator comprises an optical transmitter and receiver pair.

10. Apparatus as claimed in claim 6, wherein the signal selecting means comprises a host interface having user controls for allowing a user to create a stimulus wave signal.

11. A device as claimed in claim 6, wherein the signal selecting means comprises means for creating a signal having a desired signal characteristic and for providing a data signal corresponding to the signal characteristic of the created electrical signal.

12. A multichannel stimulator apparatus having a plurality of channels, the apparatus comprising:
   host user interface means for enabling a user to select a channel, select a stimulus wave signal for the selected channel and generate a data signal specifying the channel and stimulus wave signal;
   master means for receiving the data signal and directing it to the specified channel as a wave building instruction signal; and
   a plurality of slave units associated wtih the plurality of channels, the plurality of slave units including a slave unit associated with the channel specified and responsive to the wave building signal to generate a corresponding stimulus wave signal in the channel specified, each of said slave units including logic circuitry.

13. Apparatus as claimed in claim 12, further comprising means coupled to each of the slave units for electrically isolating the stimulus wave signal in the channel specified from other channels and for amplifying and converting the stimulus wave signal to a corresponding high fidelity current stimulus wave signal.

* * * * *